(12) United States Patent
Sullivan et al.

(10) Patent No.: US 7,666,151 B2
(45) Date of Patent: Feb. 23, 2010

(54) DEVICES AND METHODS FOR PASSIVE PATIENT MONITORING

(75) Inventors: Patrick K. Sullivan, Kailua, HI (US); Ken C. K. Cheung, Kailua, HI (US); Christopher J. Sullivan, Kailua, HI (US); Paul Pernambuco-Wise, Honolulu, HI (US); Scott Christensen, Danville, CA (US); Mike Rosenman, Honolulu, HI (US)

(73) Assignee: Hoana Medical, Inc., Honolulu, HI (US)

( * ) Notice: Subject to any disclaimer, the term of this patent is extended or adjusted under 35 U.S.C. 154(b) by 382 days.

(21) Appl. No.: 10/301,524

(22) Filed: Nov. 20, 2002

(65) Prior Publication Data

US 2004/0111045 A1    Jun. 10, 2004

(51) Int. Cl.
*A61B 5/103* (2006.01)
*A61B 5/117* (2006.01)
*A61B 5/08* (2006.01)
*G08B 23/00* (2006.01)

(52) U.S. Cl. .................. 600/587; 600/484; 600/534; 600/595; 340/573.1

(58) Field of Classification Search .............. 600/484, 600/534, 587, 595; 340/573.1
See application file for complete search history.

(56) References Cited

U.S. PATENT DOCUMENTS

| | | |
|---|---|---|
| 3,742,937 A | 7/1973 | Manuel et al. |
| 3,898,981 A | 8/1975 | Basham |
| 3,926,177 A | 12/1975 | Hardway, Jr. et al. |
| 3,996,922 A | 12/1976 | Basham |
| 4,033,332 A | 7/1977 | Hardway, Jr. et al. |
| 4,175,263 A | 11/1979 | Triplett |
| 4,245,648 A | 1/1981 | Trimmer et al. |

(Continued)

FOREIGN PATENT DOCUMENTS

DE    3531399    3/1986

(Continued)

OTHER PUBLICATIONS

"Measurement Specialties, Inc.—The Leader in Sensor Technology" Sensor Products Division, P.O. Box 799 Valley Forge, PA 19842-0799, USA, Telephone: 610-650-1500, Fax: 610-650-1509, Downloaded from Internet <<http://www.msiusa.com/default/index.asp>> (Apr. 28, 2003)1 page total.

(Continued)

*Primary Examiner*—Max Hindenburg
*Assistant Examiner*—Jeffrey G Hoekstra
(74) *Attorney, Agent, or Firm*—Fulwider Patton LLP

(57) ABSTRACT

Devices, systems and methods provide passive patient monitoring of such parameters as body motion, body position, respiratory rate and/or heart rate. Passive monitoring generally involves a sensor device having at least two piezoelectric sensors, provided on a surface, such as a bed, chair, operating table or the like, so that a patient may be coupled with the device by simply allowing the patient to lie, sit, lean, stand on or wear the surface. In one embodiment, multiple patients in a general care area of a hospital may be continuously monitored via multiple passive monitoring devices. If a patient fails to meet one or more predefined threshold criteria or has a negative physiological trend, the system may activate an alarm.

82 Claims, 13 Drawing Sheets

U.S. PATENT DOCUMENTS

| | | |
|---|---|---|
| 4,320,766 A | 3/1982 | Alihanka et al. |
| 4,359,726 A | 11/1982 | Lewiner et al. |
| 4,365,130 A | 12/1982 | Christensen |
| 4,381,788 A | 5/1983 | Douglas |
| 4,403,215 A | 9/1983 | Hofmann et al. |
| 4,428,380 A | 1/1984 | Wong et al. |
| 4,429,699 A | 2/1984 | Hatschek |
| 4,438,771 A | 3/1984 | Friesen et al. |
| 4,446,869 A | 5/1984 | Knodle |
| 4,459,991 A | 7/1984 | Hatschek |
| 4,474,185 A | 10/1984 | Diamond |
| 4,475,557 A | 10/1984 | Hatschek et al. |
| 4,494,553 A | 1/1985 | Sciarra et al. |
| 4,509,527 A * | 4/1985 | Fraden ............... 600/484 |
| 4,513,748 A | 4/1985 | Nowogrodzki et al. |
| 4,537,200 A | 8/1985 | Widrow |
| 4,539,560 A | 9/1985 | Fleck |
| 4,562,723 A | 1/1986 | Hubner |
| RE32,180 E | 6/1986 | Lewiner et al. |
| 4,595,016 A | 6/1986 | Fertig et al. |
| 4,628,939 A | 12/1986 | Little et al. |
| 4,633,237 A | 12/1986 | Tucknott |
| 4,657,026 A | 4/1987 | Tagg |
| 4,660,564 A | 4/1987 | Benthin et al. |
| 4,684,767 A | 8/1987 | Phalen |
| 4,686,999 A | 8/1987 | Snyder et al. |
| 4,695,955 A * | 9/1987 | Faisandier ............... 600/300 |
| 4,734,044 A | 3/1988 | Radice |
| 4,757,825 A | 7/1988 | Diamond |
| 4,773,422 A | 9/1988 | Isaacson et al. |
| 4,827,763 A | 5/1989 | Bourland et al. |
| 4,845,323 A | 7/1989 | Beggs |
| 4,862,144 A | 8/1989 | Tao |
| 4,889,131 A | 12/1989 | Salem et al. |
| 4,907,845 A | 3/1990 | Wood |
| 4,926,866 A | 5/1990 | Lee |
| 4,967,760 A | 11/1990 | Bennett, Jr. et al. |
| 4,989,611 A | 2/1991 | Zanetti et al. |
| 5,002,060 A | 3/1991 | Nedivi |
| 5,012,815 A | 5/1991 | Bennett, Jr. et al. |
| 5,036,859 A | 8/1991 | Brown |
| 5,137,033 A * | 8/1992 | Norton ............... 128/886 |
| 5,144,284 A * | 9/1992 | Hammett ............... 340/573.1 |
| 5,148,002 A | 9/1992 | Kuo et al. |
| 5,184,112 A | 2/1993 | Gusakov |
| 5,235,319 A | 8/1993 | Hill |
| 5,241,964 A | 9/1993 | McQuilkin |
| 5,253,656 A | 10/1993 | Rincoe |
| 5,276,432 A | 1/1994 | Travis |
| 5,292,340 A | 3/1994 | Crosby et al. |
| 5,309,916 A | 5/1994 | Hatschek |
| 5,353,012 A | 10/1994 | Barham |
| 5,393,935 A | 2/1995 | Hasty |
| 5,429,399 A | 7/1995 | Geringer |
| 5,448,996 A | 9/1995 | Bellin et al. |
| 5,479,932 A | 1/1996 | Higgins et al. |
| 5,490,516 A | 2/1996 | Hutson |
| 5,515,865 A | 5/1996 | Scanlon |
| 5,544,651 A | 8/1996 | Wilk |
| 5,590,649 A | 1/1997 | Caro et al. |
| 5,590,650 A | 1/1997 | Genova |
| 5,620,003 A | 4/1997 | Sepponen |
| 5,623,760 A | 4/1997 | Newham |
| 5,633,627 A | 5/1997 | Newham |
| 5,684,460 A | 11/1997 | Scanlon |
| 5,724,025 A | 3/1998 | Tavori |
| 5,724,990 A | 3/1998 | Ogino |
| 5,807,267 A | 9/1998 | Bryars et al. |
| 5,808,552 A * | 9/1998 | Wiley et al. ............... 340/573.4 |
| 5,844,488 A | 12/1998 | Musick |
| 5,846,206 A | 12/1998 | Bader |
| 5,853,005 A | 12/1998 | Scanlon |
| 5,902,255 A | 5/1999 | Ogino |
| 5,942,979 A | 8/1999 | Luppino |
| 5,964,720 A | 10/1999 | Pelz |
| 5,989,193 A | 11/1999 | Sullivan |
| 6,014,346 A * | 1/2000 | Malone ............... 368/10 |
| 6,047,203 A | 4/2000 | Sackner et al. |
| 6,050,940 A | 4/2000 | Braun et al. |
| 6,067,019 A | 5/2000 | Scott |
| 6,068,589 A | 5/2000 | Neukermans |
| 6,078,261 A | 6/2000 | Davsko |
| 6,133,837 A | 10/2000 | Riley |
| 6,146,332 A | 11/2000 | Pinsonneault et al. |
| 6,195,008 B1 | 2/2001 | Bader |
| 6,198,394 B1 | 3/2001 | Jacobsen et al. |
| 6,208,250 B1 | 3/2001 | Dixon |
| 6,248,064 B1 | 6/2001 | Gopinathan et al. |
| 6,252,512 B1 | 6/2001 | Riley |
| 6,261,237 B1 | 7/2001 | Swanson et al. |
| 6,280,392 B1 * | 8/2001 | Yoshimi et al. ............... 600/534 |
| 6,297,738 B1 * | 10/2001 | Newham ............... 340/573.1 |
| 6,312,387 B1 | 11/2001 | Nissila et al. |
| 6,315,719 B1 | 11/2001 | Rode et al. |
| 6,375,621 B1 | 4/2002 | Sullivan |
| 6,402,691 B1 | 6/2002 | Peddicord et al. |
| 6,413,223 B1 | 7/2002 | Yang et al. |
| 6,415,033 B1 | 7/2002 | Halleck et al. |
| 6,425,872 B1 | 7/2002 | Hagiwara et al. |
| 6,440,082 B1 | 8/2002 | Joo et al. |
| 6,443,907 B1 | 9/2002 | Mansy et al. |
| 6,445,299 B1 | 9/2002 | Rojas, Jr. |
| 6,450,957 B1 * | 9/2002 | Yoshimi et al. ............... 600/309 |
| 6,475,153 B1 | 11/2002 | Khair et al. |
| 6,485,441 B2 | 11/2002 | Woodward |
| 6,491,647 B1 | 12/2002 | Bridger et al. |
| 6,494,829 B1 | 12/2002 | New, Jr. et al. |
| 6,497,658 B2 | 12/2002 | Roizen et al. |
| 6,506,153 B1 | 1/2003 | Littek et al. |
| 6,517,497 B2 | 2/2003 | Rymut et al. |
| 6,540,673 B2 | 4/2003 | Gopinathan et al. |
| 6,547,743 B2 | 4/2003 | Brydon |
| 6,554,773 B1 | 4/2003 | Nissila et al. |
| 6,565,515 B2 | 5/2003 | Ogura |
| 6,575,902 B1 | 6/2003 | Burton |
| 6,575,915 B2 | 6/2003 | Nissilä et al. |
| 6,575,916 B2 | 6/2003 | Halleck et al. |
| 6,579,232 B2 | 6/2003 | Sakamaki et al. |
| 6,583,727 B2 | 6/2003 | Nunome |
| 6,585,645 B2 | 7/2003 | Hutchinson |
| 6,599,251 B2 | 7/2003 | Chen et al. |
| 6,600,949 B1 | 7/2003 | Turcott |
| 6,648,828 B2 | 11/2003 | Friedman et al. |
| 6,652,466 B2 | 11/2003 | Sugo et al. |
| 6,689,069 B2 | 2/2004 | Bratteli et al. |
| 6,696,653 B1 | 2/2004 | Smith |
| 6,702,752 B2 | 3/2004 | Dekker |
| 6,727,445 B2 | 4/2004 | Cullinan |
| 6,746,403 B2 | 6/2004 | Kolluri et al. |
| 6,778,090 B2 | 8/2004 | Newham |
| 6,784,797 B2 | 8/2004 | Smith |
| 6,791,460 B2 | 9/2004 | Dixon |
| 6,804,656 B1 | 10/2004 | Rosenfeld et al. |
| 6,897,780 B2 | 5/2005 | Ulrich |
| 6,917,293 B2 | 7/2005 | Beggs |
| 6,984,207 B1 | 1/2006 | Sullivan |
| 6,988,989 B2 | 1/2006 | Weiner et al. |
| 2002/0019584 A1 | 2/2002 | Schulze et al. |
| 2003/0018241 A1 | 1/2003 | Mannheimer |
| 2004/0111296 A1 | 6/2004 | Rosenfeld et al. |
| 2005/0159987 A1 | 7/2005 | Rosenfeld et al. |
| 2005/0177400 A1 | 8/2005 | Rosenfeld et al. |
| 2005/0187796 A1 | 8/2005 | Rosenfeld et al. |

| | | |
|---|---|---|
| 2005/0203777 A1 | 9/2005 | Rosenfeld et al. |

FOREIGN PATENT DOCUMENTS

| | | |
|---|---|---|
| EP | 0034077 | 8/1981 |
| GB | 2138144 A | 10/1984 |
| GB | 2166871 A | 5/1986 |
| GB | 2252827 | 8/1992 |
| JP | 11267106 | 10/1999 |
| JP | 2000316915 | 11/2000 |
| JP | 2001070256 | 3/2001 |
| JP | 2001145605 | 5/2001 |
| JP | 2001353134 | 12/2001 |
| JP | 2002052010 | 2/2002 |
| JP | 2002143101 | 5/2002 |
| JP | 2002224051 | 8/2002 |
| WO | WO 96/36279 | 11/1996 |
| WO | WO 98/52467 | 11/1998 |
| WO | WO 01/64103 A1 | 9/2001 |
| WO | WO 01/78601 A1 | 10/2001 |
| WO | WO 03/082111 A1 | 10/2003 |
| WO | 2005/000108 A2 | 1/2005 |

OTHER PUBLICATIONS

"Measurement Specialties, Inc.—Piezoelectric Polymer" Sensor Products Division, P.O. Box 799 Valley Forge, PA 19842-0799, USA, Telephone: 610-650-1500, Fax: 610-650-1509, Downloaded from Internet <<http://www.msiusa.com/piezo/index.htm>> (Apr. 28, 2003) 1 page total.

"Measurement Specialties, Inc.—Piezo Coax Cable" Sensor Products Division, P.O. Box 799 Valley Forge, PA 19842-0799, USA, Telephone: 610-650-1500, Fax: 610-650-1509, Downloaded from Internet <<http://www.msiusa.com/piezo/piezo_coax_cable.htm>> (Apr. 28, 2003) 1 page total.

"Nellcor—Complete Solutions for your Clinical Needs" Nellcor, 4280 Hacienda Drive, Pleasanton, CA 94588, USA, Telephone: 800-635-5267, Downloaded from Internet: <<http://www.nellcor.com/>> (Apr. 28, 2003) 1 page total.

"Nellcor—Pulse Oximetry" Nellcor, 4280 Hacienda Drive, Pleasanton, CA 94588, USA, Telephone: 800-635-5267, Downloaded from Internet: <<http://www.nellcor.com/prod/List.aspx?S1=POX&S2=SEN>> (Apr. 28, 2003) 1 page total.

"Nellcor—Oximax® Sensors" Nellcor, 4280 Hacienda Drive, Pleasanton, CA 94588, USA, Telephone: 800-635-5267, Downloaded from Internet: <<http://www.nellcor.com/prod/Product.aspx?S1=POX&S2=SEN&id=255>> (Apr. 28, 2003) 2 pages total.

Product Brochure: Measurement Specialties, Inc., Sensor Products Division, P.O. Box 799 Valley Forge, PA 19842-0799, USA, Telephone: 610-650-1500, Fax: 610-650-1509, 5 pages total.

J. Siivola, *New Noninvasive Piezoelectric Transducer for Recording of Respiration, Heart Rate and Body Movements*, Medical & Biological Engineering & Computing, vol. 27, No. 4, Jul. 1989, pp. 423-424.

Contract Agreement between The Henry M. Jackson Foundation for the Advancement of Military Medicine and Oceanit Laboratories, Inc. (Effective Date: Jan. 10, 1997) 36 pages total.

M. Scanlon, *Acoustic Sensor for Health Status Monitoring*, 1998, IRIS Acoustic and Seismic Sensing, vol. II, pp. 205-222.

Bass et al., *Getting Two Birds with One Phone: An acoustic sensor for both speech recognition and medical monitoring*, 138th Meeting of the Acoustical Society of America, Columbus, Ohio Nov. 2, 1999.

Subaward Agreement between The Henry M. Jackson Foundation for the Advancement of Military Medicine and Oceanit Laboratories, Inc. (Effective Date: Apr. 17, 2001) 19 pages total.

Office Action mailed Aug. 28, 2009, in connection with Japanese Patent Application No. 2004-553965.

\* cited by examiner

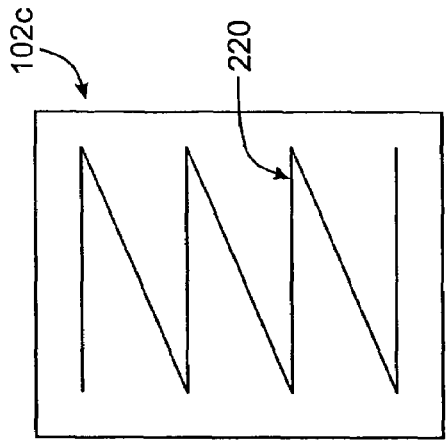
FIG. 2A
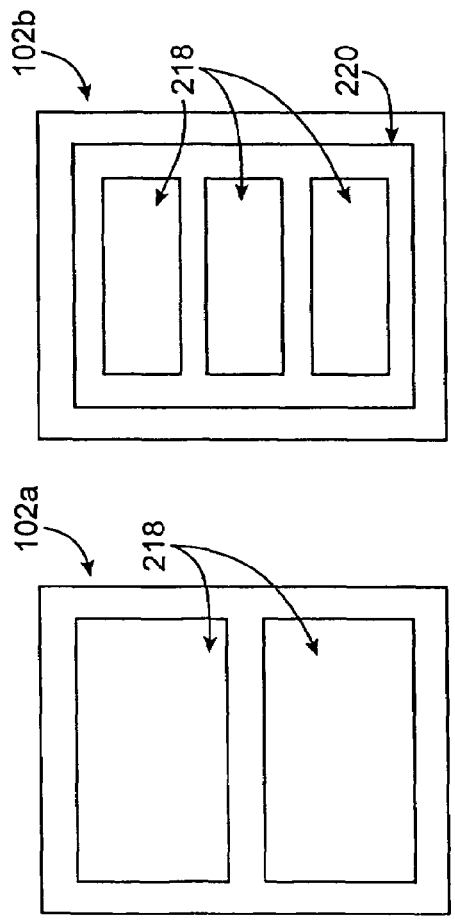
FIG. 2B
FIG. 2C
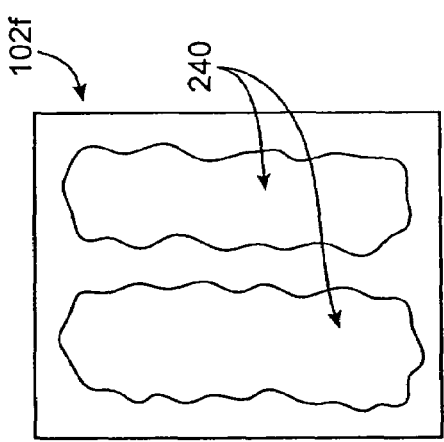
FIG. 2D
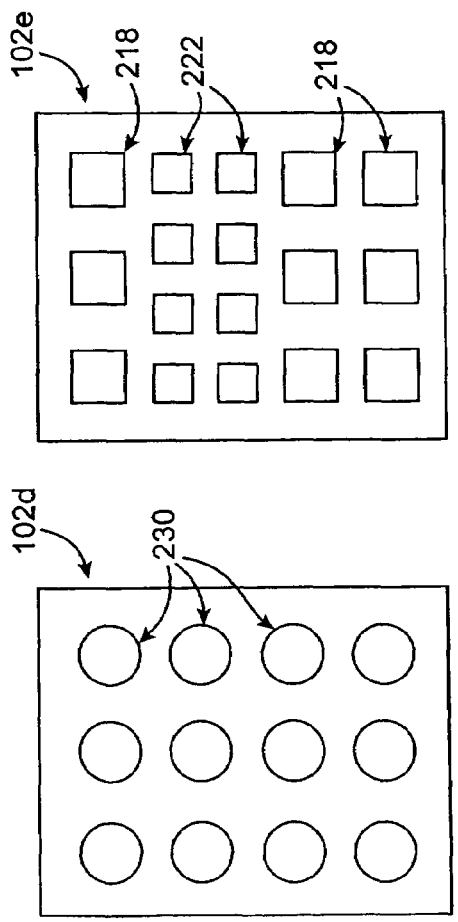
FIG. 2E
FIG. 2F

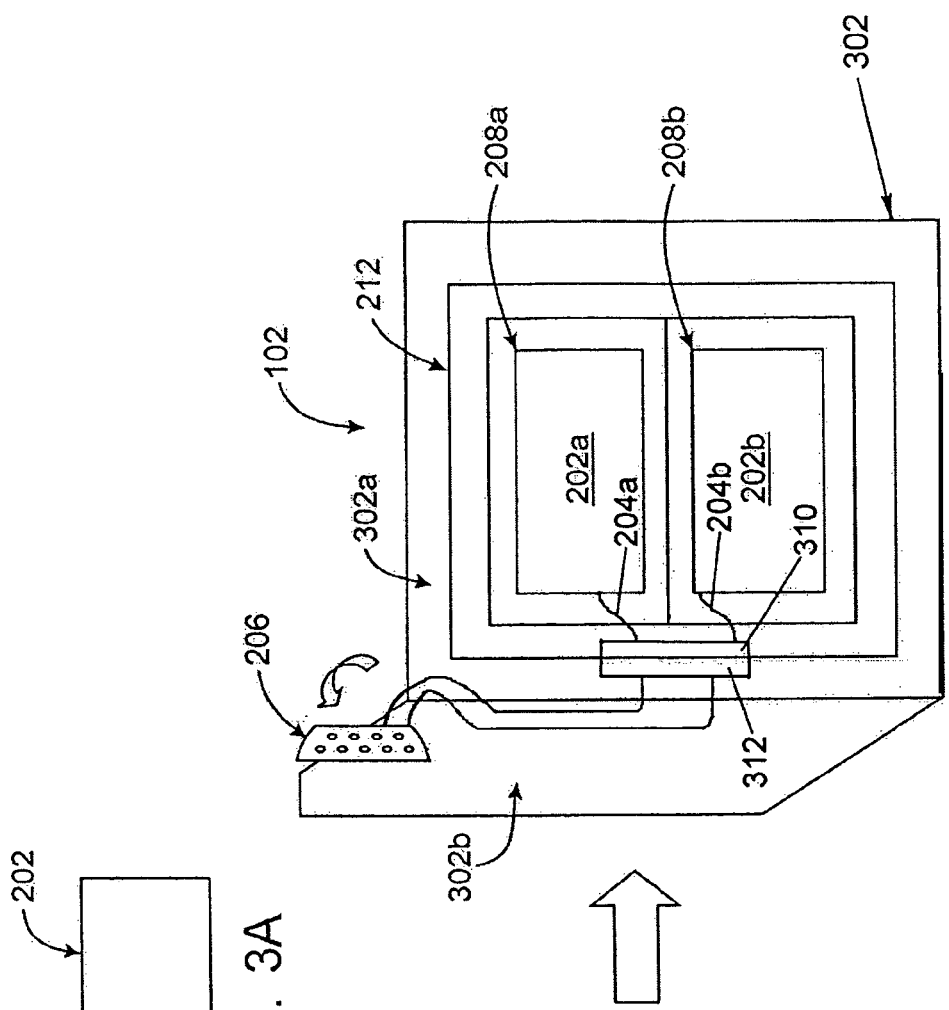
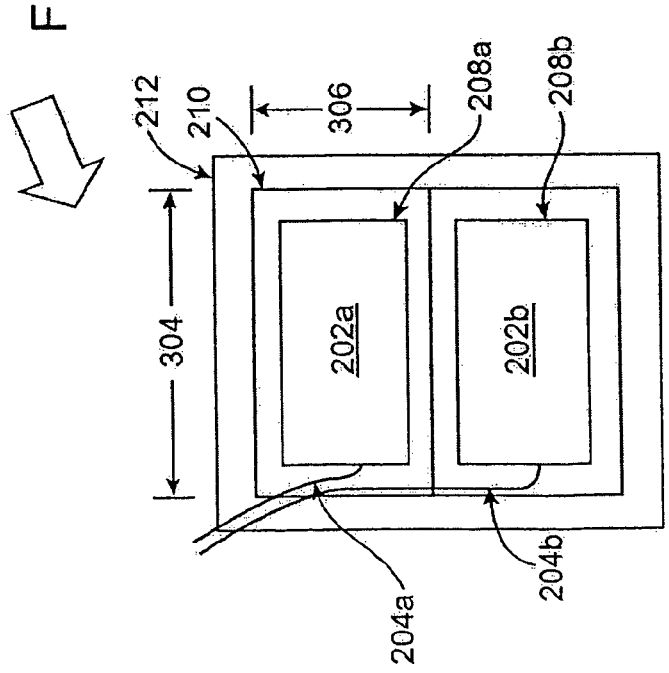
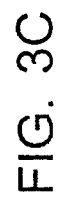
FIG. 3A
FIG. 3B
FIG. 3C

DEVICES AND METHODS FOR PASSIVE PATIENT MONITORING

BACKGROUND OF THE INVENTION

The present invention relates generally to medical devices, systems and methods. More specifically, the invention relates to devices, systems and methods for passive patient monitoring.

Monitoring patients is an important aspect of patient care in many different settings. In a general care floor or ward of a hospital, for example, monitoring vital physiological signs such as respiratory rate, heart rate and blood pressure is a basic component of patient care. Monitoring the presence or absence of a patient in a hospital bed or in a chair in the patient's hospital room and monitoring patient movement on that bed or chair may also be beneficial in a general care ward or other area of a hospital. If certain patients leave their beds, they run a risk of falling and injuring themselves. If a patient stops moving in bed, it may mean that the patient is dying, is in a coma or is suffering from a medical complication that makes movement difficult or impossible and requires attention. Excessive movement may indicate a seizure or other condition.

Patients in general care areas of hospitals are typically monitored only intermittently, due to practical difficulties such as lack of staff and resources. Vital signs of a patient on a general care floor, for example, are typically taken every 3-4 hours by a nurse or medical technician. At the same time, as the population ages and hospital admissions are postponed by HMOs and other managed care providers, the severity of hospital patient health problems increases and the number of patients overall increases. Thus, hospital populations continue to increase and hospital patients typically require closer monitoring than they did in the past. A significant and expanding nursing shortage, however, makes increased direct patient monitoring through increased staffing impractical, if not impossible.

Physiological monitoring is equally important in other settings. For example, when a patient undergoes a surgical procedure under conscious sedation, such as in an outpatient operating suite in a hospital or surgi-center, or in a procedure room of a physician's private clinic, the patient's respiratory and heart rates should be continuously monitored. Standards set by the Joint Committee for Accreditation of Healthcare Organizations (JCAHO) require such continuous monitoring of respiratory and heart rates, to detect and prevent adverse effects of sedating medications on patients undergoing procedures under conscious sedation. Other contexts in which physiological monitoring may be important include infant monitoring to detect early signs of sudden infant death syndrome (SIDS), operating room patient monitoring, monitoring of patients during emergency transport, nursing home and skilled nursing facility patient monitoring, home monitoring and the like.

Failing to adequately monitor patients may have grave consequences in any of a number of settings. In a hospital, elderly patients who should remain in bed often become disoriented, leave their beds, and sustain injuries such as fractured hips, arms or wrists. Statistics show that over 25% of elderly hip fracture patients may never leave the hospital after receiving treatment for such a fracture. Another patient may die quietly in a hospital room during a 4-hour period between monitoring checks by a nurse. The patient's family may be highly upset to learn that the death might have been prevented or at least postponed long enough for them to be present. In other examples, vital physiological functions such as lung or heart function may deteriorate significantly without detection, due to insufficient monitoring. Thus, the opportunities for adverse medical events and medical malpractice liability are pervasive on a general care ward of a hospital and in other settings where continuous, accurate patient monitoring is impractical or impossible using currently available systems.

Current systems for patient monitoring do not generally provide for convenient, constant, around-the-clock monitoring. On a general care ward of a hospital, for example, monitoring typically consists of a team of nurses circulating from patient to patient, at three- or four-hour intervals, to take vital signs such as respiratory rate and heart rate. In some hospitals, this monitoring may be augmented by one or more devices, such as a bedside pulse-oximeter, which monitors pulse and oxygen saturation via a small clamp-like device attached to a patient's finger. The pulse-oximeter may be designed to sound an alarm, if a certain pulse or oxygen threshold level is reached. One example of such a system is the Oxinet® II Central Station Network, available from Nellcor (www.nellcor.com). Pulse-oximeters do not measure respiratory rate, however, which is often one of the earliest signs of patient distress. The method for measuring respiratory rate that is most typically used in a general care hospital setting is direct observation by a nurse, certified nursing assistant or the like, which is highly inaccurate, due to the difficulty of counting respirations from merely watching a patient's chest movement. Other currently available methods for measuring respiratory rate include impedance pneumography, which is complex and rarely used outside of the neonatal intensive care unit setting, and capnography, which is also difficult and requires at least that the patient be attached to a nasal canula. Other currently available monitoring systems attempt to measure other patient parameters. These include electrocardiography (ECG) transmitters, used in a telemetry unit to monitor heart physiology in patients. ECG electrodes are attached directly to a patient's skin and a transmitter coupled with the electrodes is carried by the patient so that physiological data related to the patient's heart function can be transmitted to a central monitoring station. Blood pressure cuffs may be attached to patients and programmed to intermittently, automatically take blood pressure readings.

These currently available systems and methods for patient monitoring have several characteristics in common. Virtually all require a patient to be physically connected to a monitoring apparatus. Many, such as automatic blood pressure cuffs, provide only for intermittent monitoring. Physical connection to monitoring apparatus can be cumbersome and inconvenient for patients, sometimes leading to patient noncompliance, such as when a patient removes a device due to discomfort. Attached devices may also loosen, change position, fall partially off the patient and the like, leading to inaccurate monitoring data. Intermittent monitoring can lead to missed or late diagnosis and adverse patient outcomes, especially in very sick patients whose conditions may change rapidly.

Current systems also do not monitor patient movement or positioning, such as on a patient bed or chair. As described above, patient movement can be an essential monitoring tool. For example, complete absence of patient movement on a bed could indicate that the patient has left the bed. Relatively slight movement, a significant reduction in movement or the like could indicate that the patient is sufficiently still that some medical problem might have occurred. Significant increases in patient movement might indicate a seizure or significant patient discomfort.

Therefore, it would be advantageous to have devices, systems and methods for passively monitoring one or more patients. Such passive monitoring would ideally be continuous, but would not require inconvenient or cumbersome direct attachment of a device to a patient. It would be advantageous if such passive monitoring could detect motion and/or positioning of a patient on a surface, such as a patient bed or chair, and if respiratory rate, heart rate, and/or other physiological parameters could also be monitored. Ideally, monitoring would include activating an alarm when one or more thresholds were met or when a predefined negative trend occurred, and may also involve providing data to a user in other forms, such as for display on a monitor. It would also be desirable to provide devices and methods for monitoring multiple patients simultaneously. At least some of these objectives will be met by the present invention.

BRIEF SUMMARY OF THE INVENTION

Devices, systems and methods of the present invention provide for passive monitoring of one or more patients, infants, nursing home patients, home health care patient or any other person or people for whom monitoring may be beneficial. "Passive monitoring" generally refers to the fact that monitoring according to the invention does not require direct attachment of a device to a patient. Generally, a patient is coupled with a device of the invention by simply allowing the patient to lie, sit, lean, stand or the like on or against a surface on which the device is disposed, or in some embodiments to wear a device either next to the skin or over one or more layers of clothing. Thus, the term "passive monitoring" as it is used herein generally refers to the fact that devices of the present invention typically do not require direct attachment to a patient to monitor that patient.

In some embodiments, a sensor device of the invention includes at least two piezoelectric sensors coupled with a flat surface or pad, which may be positioned on a bed, chair seat, chair back, wheelchair, operating room table, dentist's chair or the like. The sensor device may be placed under one or more layers of bedding and may monitor the patient through one or more layers of patient clothing, a patient gown, or the like. The sensor device will typically be coupled with a processor, either by wired or wireless communication. The processor receives sensed data from the piezoelectric sensors and processes the sensed data into a form that is usable by a physician, nurse or other user. Any suitable patient parameter may be monitored, such as but not limited to patient movement, patient position, respiratory rate, heart rate, blood pressure and/or the like. Such devices may be used for one patient alone, such as a patient undergoing a procedure under conscious sedation, or may be used to monitor multiple patients simultaneously, such as multiple patients in a general care floor or ward of a hospital.

In one aspect of the present invention, a method of passively monitoring at least one patient includes providing a sensor device on a surface, the sensor device having at least two piezoelectric sensors. A patient is then coupled with at least a portion of the sensor device by allowing the patient to lie, sit, lean, stand on or wear the surface. A first mechanical signal is sensed with a first piezoelectric sensor of the sensor device, a second mechanical signal is sensed with a second piezoelectric sensor of the sensor device, the first and second mechanical signals are converted into first and second digital signals, and the first and second digital signals are compared. Finally, patient data is provided to a user based on the comparison of the digital signals.

The sensor device may be provided on any suitable surface, such as a hospital bed, a bed, an operating room table, an examining table, a procedure chair or table, a dentist's chair, a hospital chair, a chair seat, a chair back, a wheelchair, a baby's crib, a stretcher, a gurney, or any other surface. In some embodiments, the sensor device may be provided as a wearable device. Typically, in addition to at least two piezoelectric sensors, the sensor device further comprises a flat surface having means for coupling the piezoelectric sensors with the flat surface. Thus, coupling the patient with the sensor device may involve simply allowing the patient to lie on a bed on which the device is provided. In another embodiment, coupling the patient with the sensor device may involve allowing the patient to sit on a chair on which the device is provided, either on the chair seat, the chair back or both. Oftentimes, the patient will be coupled with the sensor through at least one layer of clothing, bedding or other material.

In various embodiments, any of a number of mechanical signals may be sensed by the piezoelectric sensors. In one embodiment, for example, stress signals, thermal signals and/or acoustic signals may be sensed. Such signals may be sensed in a patient or non-patient in any setting. For example, the patient may be a patient in a general care area of a hospital, in a long-term care facility or in a nursing home. In another embodiment, the patient may be undergoing a surgical procedure under conscious sedation.

A sensor device may include any suitable number of piezoelectric sensors. In various embodiments, the sensor device may include two, four, six, eight, sixteen, eighteen, thirty-two or thirty-six piezoelectric sensors. Any number, combination, pattern, size, shape or type of piezoelectric sensors is contemplated. Where more than two sensors are included in the sensor device, any combination of sensors may be used to sense mechanical signals and any combination of signals from various sensors may be compared to provide patient data to a user. For example, a method may include sensing third and fourth mechanical signals with third and fourth piezoelectric sensors, converting the third and fourth mechanical signals into third and fourth digital signals, and comparing the first, second, third and fourth digital signals.

Comparing the digital signals may include comparing either presence or absence of one signal with presence or absence of another signal. For example, if there is a positive mechanical signal in one sensor and no signal in another sensor, this may be used to provide information regarding a patient's position on a sensor device. Comparing the digital signals may further comprise comparing quantity, quality and/or information content of the first signal with quantity, quality and/or information content of the second signal. For example, a mechanical signal from a sensor positioned near a patient's chest that corresponds to a heart beat signal may have a higher quality than a heart beat signal from a sensor positioned near the patient's right foot. In one embodiment, a method further includes selecting one signal over other signals to provide as data to a user, based on which of the signals has the highest quality or information content. Optionally, a method may also include determining, based on the comparison of two or more signals, presence or absence of the patient on the surface. The method may further include determining a position of the patient on the surface.

In one embodiment, the method involves grouping the digital signals into at least two groups corresponding to at least two patient parameters. For example parameters may include but are not limited to patient motion on the sensor device, patient position on the sensor device, patient respiratory rate and/or patient heart rate. Optionally, the method may include comparing at least one of the digital signals to at least one predefined threshold. Such thresholds may involve any patient parameter or combination of parameters. For example, one or more patient body motion digital signals may be compared with at least one of a minimum amount of body motion and a maximum amount of body motion. In another embodiment, one or more respiratory rate digital signals may be compared with at least one of a minimum respiratory rate and a maximum respiratory rate. In still another embodiment, one or more heart rate digital signals may be compared with at least one of a minimum heart rate and a maximum heart rate. In other embodiments, other signals or a combination of signals may be compared with multiple thresholds. Where thresholds are used, providing patient data to a user may comprise activating an alarm when at least one digital signal does not meet at least one predefined threshold. In other embodiments, an alarm may be activated if a negative trend is detected in one or more patient parameters. For example, a heart beat signal may be compared with earlier heart beat signals and a respiratory signal may be compared with earlier respiratory signals and an alarm may be activated if there is a negative heart beat trend, a negative respiratory trend or some combination thereof.

Patient data may be provided to one or more users in any suitable form. For example, providing patient data may comprise activating an alarm based on the comparison of the digital signals. In some embodiments, providing patient data may further comprise providing a position of the patient on the surface. In other embodiments, providing patient data to a user may include providing a respiratory rate of the patient, a heart rate of the patient or both. In some embodiments, such as in a general care area of a hospital, in a long-term care facility or in a nursing home, multiple patients are monitored simultaneously, and providing patient data comprises providing data at a common location. For example, the common location may include, but is not limited to a nursing station, a display monitor, a digital pager, a wireless handheld device, an existing nurse call station and/or a monitoring room.

In another aspect, a method of passively monitoring physiology of multiple patients includes first providing multiple sensor devices on multiple surfaces, each sensor device having at least two piezoelectric sensors. Each of the patients is coupled with at least a portion of one of the sensor devices by allowing each patient to lie, sit, lean, stand on or wear one of the surfaces. At least one mechanical signal is sensed with at least two of the piezoelectric sensors on each sensor device, and the sensed mechanical signals are converted into digital signals. Digital signals corresponding to at least two of the piezoelectric sensors are then compared for each patient; and patient data corresponding to the multiple patients is provided to a user at a central location, based on the comparison of the digital signals.

In yet another aspect, apparatus for passively monitoring a patient includes a surface for coupling with the patient and at least two piezoelectric sensors coupled with the surface for sensing at least one mechanical signal from the patient. A processor is coupled with the piezoelectric sensors for converting the at least one mechanical signal into at least one digital signal and for comparing digital signals corresponding to each of the at least two piezoelectric sensors to provide data pertaining to the patient. A first connector couples the piezoelectric sensors with the processor and a second connector is provided for coupling the processor with apparatus for providing the patient data to a user.

In some embodiments, the surface comprises a flat pad. For example, the flat pad may comprise at least one layer of a resilient foam material. The piezoelectric sensors may be disposed along the surface in any suitable pattern for enabling monitoring of a patient. Surfaces may have any suitable dimensions. In one embodiment, the surface has dimensions to allow the surface to be positioned on at least one of a chair seat and a chair back for monitoring the patient during a surgical procedure under conscious sedation. In other embodiments, dimensions of the surface may allow the surface to be positioned on a crib or a bed for monitoring an infant. In still another embodiment, dimensions of the surface may allow the surface to be positioned on a bed for monitoring the patient in a hospital or nursing home.

Optionally, the apparatus may further include a sheath for containing at least a portion of the surface to provide a protective layer between the surface and the patient. Typically, such a sheath will be water resistant. Sometimes, the sheath includes at least one connector for connecting the sheath with the surface, and the surface must be connected with the connector in order to monitor the at least one mechanical signal of the patient. In some embodiments, the sheath is disposable after being used to monitor one patient.

The piezoelectric sensors may be fabricated from any suitable material. In some embodiments, for example, the sensors comprise one or more of polyvinylidene fluoride film, polyvinylidene cable, piezoelectric ceramic discs and piezoelectric foam. The sensor device may be provided on a flat surface of a bed, and at least one mechanical signal of the patient may be monitored when the patient lies on the surface. The mechanical signal may include any suitable signal or combination of signals, but in one embodiment includes stress signals, thermal signals and/or acoustic signals.

The first connector and second connector, may include any suitable connectors. In some embodiments both connectors are wired connectors, in some embodiments they are both wireless, and in other embodiments the connectors comprise a combination of wired and wireless connectors. In one embodiment, the first connector may include means for detecting either a type of sensor device attached to the processor via the first connector or a number of times the sensor has been used. For example, when the sensor device is connected to the processor via the first connector, the connector may detect whether the device is of a type that is compatible with the processor and/or how many times the device has been used. In some embodiments, the first connector may then activate the sensor device, based on one or more criteria that it has detected.

Generally, the processor may provide patient data in any suitable form or in multiple forms. For example, patient data may be provided by activating an alarm. In one embodiment, the processor activates an alarm if the comparison of the digital signals suggests that the patient is not moving on the surface, the patient is not in contact with the surface, or the patient is moving excessively on the surface. In another embodiment, the processor activates an alarm if a respiratory rate of the patient falls below a predefined minimum respiratory rate or rises above a predefined maximum respiratory rate. In yet another embodiment, the processor activates an alarm if a heart rate of the patient falls below a predefined minimum heart rate or rises above a predefined maximum heart rate. In other embodiments, an alarm may be activated if any combination of the above occurs. Some embodiments alert an alarm if a negative trend occurs, such as a negative heart rate, respiratory rate, patient movement or other trend or combination of trends. In some embodiments, the processor further provides the patient data in the form of a patient respiratory rate, heart rate or both.

In another aspect, a disposable sheath for containing at least a portion of a sensor device for passively monitoring a patient includes a flat surface for coupling with the patient and at least one housing for containing at least a portion of the sensor device. The sheath is water resistant in some embodiments. In some embodiments, the sheath includes at least one connector for removably connecting the sheath with the apparatus for passively monitoring physiology, and connecting the sheath to the apparatus allows the apparatus to be activated to monitor the physiology of the patient.

In another aspect, a system for passively monitoring multiple patients comprises a plurality of sensor devices, each sensor device having a surface for coupling with the patient and at least two piezoelectric sensors coupled with the surface for sensing at least one mechanical signal from a patient. The system also includes a plurality of processors, each processor coupled with one sensor device for converting the at least one mechanical signal into at least one digital signal and for comparing digital signals corresponding to each of the at least two piezoelectric sensors to provide data pertaining to the patient. Finally, the system includes at least one connector coupled with each processor for connecting each processor with a common apparatus for providing the patient data for the multiple patients to a user. In various embodiments, this system may include any one or more of the features of the apparatus described above.

BRIEF DESCRIPTION OF THE DRAWINGS

FIGS. 2A-F are schematic frontal views of various embodiments of a sensor device according to various embodiments of the present invention.

FIG. 3A is a frontal view of piezoelectric sensor and transmitter for use in a sensor device, according to an embodiment of the present invention.

FIG. 3B is a frontal view of a surface for holding two piezoelectric sensors as in FIG. 3A, according to an embodiment of the present invention.

FIG. 3C is a frontal view of a complete sensor device, including a sheath for holding the surface and piezoelectric sensors of FIGS. 3A and 3B.

DETAILED DESCRIPTION OF THE INVENTION

Figure 1:
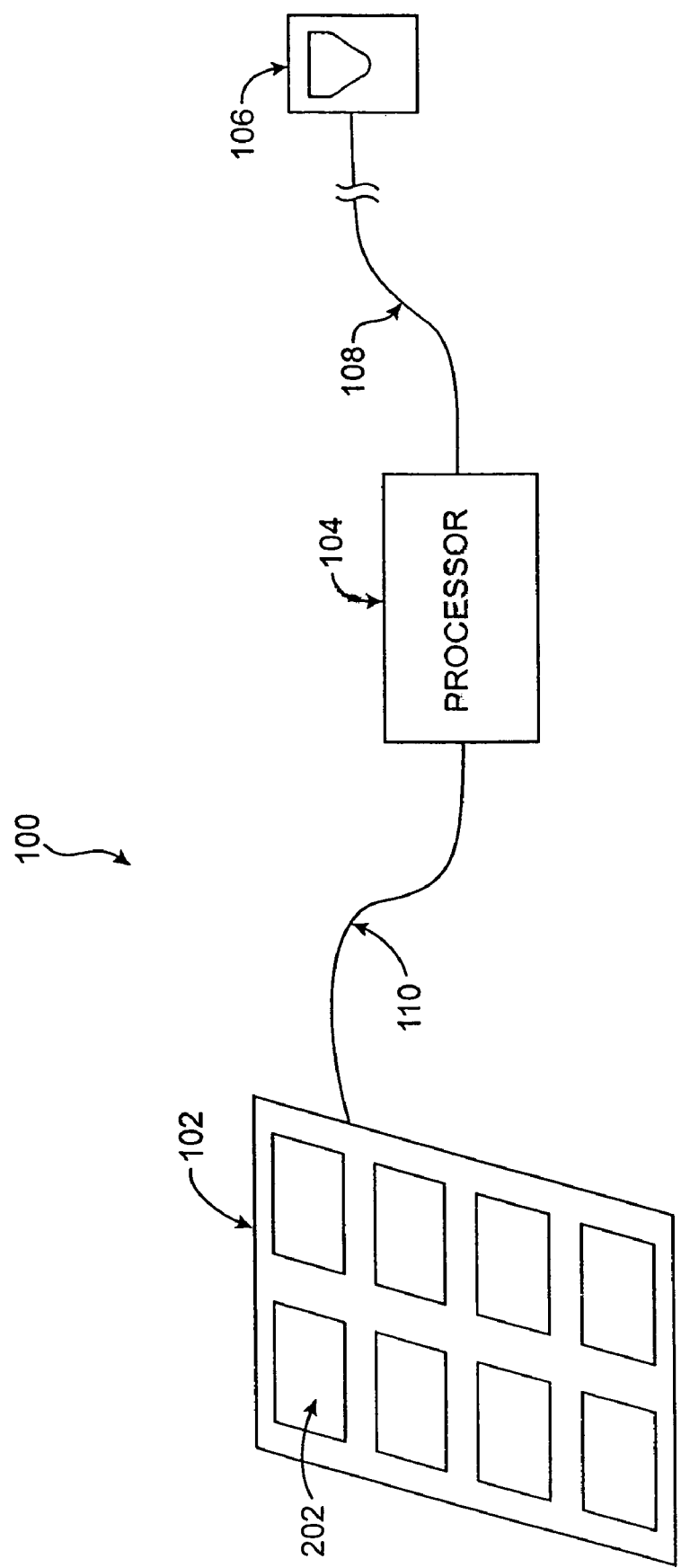
FIG. 1 is a schematic diagram of a system for passive patient monitoring, according to an embodiment of the present invention.

The present invention generally provides devices, systems and methods for passive monitoring of one or more patients, infants, nursing home residents or any other person or group of persons for whom monitoring is desired. Devices generally include a sensor device having at least two piezoelectric sensors for sensing one or more mechanical signals from a patient, a processor coupled with the sensor device for processing mechanical signals to provide patient data, and means for coupling the processor with a device for providing the data to the user. In some systems, multiple sensor devices and processors may be used to monitor multiple patients simultaneously and each processor may be coupled with a common apparatus for providing the patient data to the user.

Methods generally include providing a sensor device on a surface, coupling a patient with the device by allowing the patient to lie, sit, lean, stand on or wear the surface, sensing at least one mechanical signal with a first piezoelectric sensor, processing the signal and providing data to a user based on the processed signal. The phrase "passive patient monitoring" or simply "passive monitoring" generally refers to the idea that methods and devices of the present invention generally provide for monitoring a patient by allowing the patient to lie, sit, lean, stand or the like against a surface on which a sensor device is disposed, or possibly to comfortably wear a sensor device. Such monitoring is "passive" because it does not require directly, physically attaching one or more devices to the patient. In essence, a patient may often be monitored using devices, methods and/or systems of the present invention without even realizing that a monitoring device is in place. Typically, sensor devices of the present invention may be placed under one or more layers of sheets or other bedding and can sense patient parameters through the bedding as well as a patient gown or other clothing. Thus, methods and devices of the invention may sometimes be referred to as "invisible" as well as passive, since they may be hidden beneath bedding, within a seat cushion, or the like.

In general, any of a number of parameters or combinations of parameters relating to a patient or other monitored person may be measured. In one embodiment, for example, patient position and/or motion on a hospital bed is monitored. Optionally, patient respiratory rate and/or heart rate may also be monitored. Other parameters such as blood pressure, cardiac output, body temperature and changes in temperature, and/or the like may also suitably be sensed and monitored in various embodiments. Any such patient parameters may be monitored in any suitable person or people in any suitable setting. For example, multiple patients in a general care area of a hospital, a patient undergoing a surgical procedure under conscious sedation, patients in an emergency room or operating room, nursing home or long-term care patients, a sleeping infant, or even a home healthcare patient may be monitored. Similarly, a person may be monitored while lying on a hospital bed, a conventional bed, an operating table or a stretcher or gurney, while sitting on a chair or wheelchair, or while lying, leaning or standing on any other suitable surface. Therefore, although the following description often focuses on the exemplary embodiment of monitoring multiple patients on a general care floor or ward of a hospital, this description is used for exemplary purposes only and should not be interpreted to limit the scope of the invention as set forth in the claims.

Patient monitoring data may be provided to a user in any suitable form. In some embodiments, data is used to activate an alarm. For example, an alarm may be activated if a sensed signal from a patient goes above or below a predetermined threshold or represents a negative trend, if a combination of patient parameters (such as respiratory rate, heart rate and body motion) meets a predefined definition of a negative trend, or the like. In other embodiments, data may be provided on a monitor for a healthcare worker or other user to read. In other embodiments, data may be used to both activate an alarm and provide a display on a monitor. An alarm, display monitor or the like may provide a user with information about one patient or about multiple patients. For example, an alarm and/or a display monitor may be located in a common nursing station on a ward of a hospital, to provide one or more nurses at that station with information regarding patients throughout the ward. In other embodiments, data may be provided at a patient's bedside or may be provided both at the bedside and at a central location. Any other suitable configuration for providing physiological data to one or more users is contemplated, such as providing physiological data via one or more digital pagers, wireless handheld devices or the like. For the purposes of this patent application, the phrase "data display device" or "display device" means any means for providing physiological data to a user, such as an alarm, a monitor, an alarm and monitor, or any other suitable means.

Again, devices, systems and methods of the present invention may be used in any suitable setting for patient care, research, veterinary medicine and/or the like. In one embodiment, multiple patients on a general care floor of a hospital are passively monitored simultaneously to provide continuous monitoring without requiring the presence of a healthcare professional at each patient's bedside. Such a monitoring system may be used in any suitable floor, ward or area of a hospital or clinic. In another embodiment, the physiology of a patient undergoing a surgical procedure under conscious sedation is monitored. Apparatus, systems and methods of the invention may be used to monitor sleeping infants who may be susceptible to sudden infant death syndrome, residents in a nursing home, long-term care facility or skilled nursing facility, patients being transported in an emergency medical setting, home health care patients or any other suitable patients or non-patients. Additionally, various embodiments of the invention may be added to existing patient monitoring systems and/or may be used with other, compatible monitoring systems as original equipment manufacturer subsystems. For example, one embodiment may include multiple sensor devices and multiple processors, the latter of which all connect to an existing nurse call station system for providing patient data to one or more nurses at a common location.

Referring now to FIG. 1, a system 100 for passive patient monitoring suitably includes a sensor device 102 having at least two piezoelectric sensors 202, coupled with a processor 104, which is in turn coupled with a data display device 106 for providing physiological data to a user. Generally, sensor 102 may be coupled with processor 104 via any suitable connector 110 (or multiple connectors), such as a cable, wire, wireless transmitter or the like. Similarly, any suitable connector 108 may be used for coupling processor 104 with data display device 106. Any given embodiment may include multiple sensors 102, multiple processors 104 and/or multiple display devices 106. For example, multiple patients may be monitored simultaneously, each patient corresponding to a separate sensor device 102. In some embodiments, each sensor device 102 is coupled with its own, separate processor 104, while in other embodiments multiple sensor devices 102 may be coupled with a common processor 104. In still other embodiments, a portion of processor 104 may include separate units for each sensor, while another portion of processor 104 may include a central unit, such as a central computer. Similarly, display device 106 may comprise one, common display monitor, alarm or the like, but alternatively may comprise multiple alarms, displays, digital pagers, wireless devices or the like. Thus, various embodiments of system 100 may include one sensor device 102, one processor 104 and one display device 106, but may alternatively comprise a plurality of one or more of these components. Connectors 108, 110 may similarly be provided as single or multiple components in various embodiments.

Some embodiments of the invention are provided as portions of system 100 shown in FIG. 1. In some embodiments, for example, sensor device 102 alone is provided to a user, for example if the user already owns processor 104 and display device 106 or alternative, compatible processor and display devices. Another embodiment of the invention includes sensor device 102 and an add-on processor 104. An add-on processor 104, for example, may comprise software or hardware which may be added to an existing computer, bedside monitor or the like, to provide for processing of data received from sensor device 102. Thus, although system 100 includes sensor device 102, processor 104, display device 106 and connectors 108, 110 in one embodiment, other embodiments may include fewer elements or additional elements without departing from the scope of the invention. Each of the various elements of the invention shown in FIG. 1 is described in more detail below.

Figure 1A:
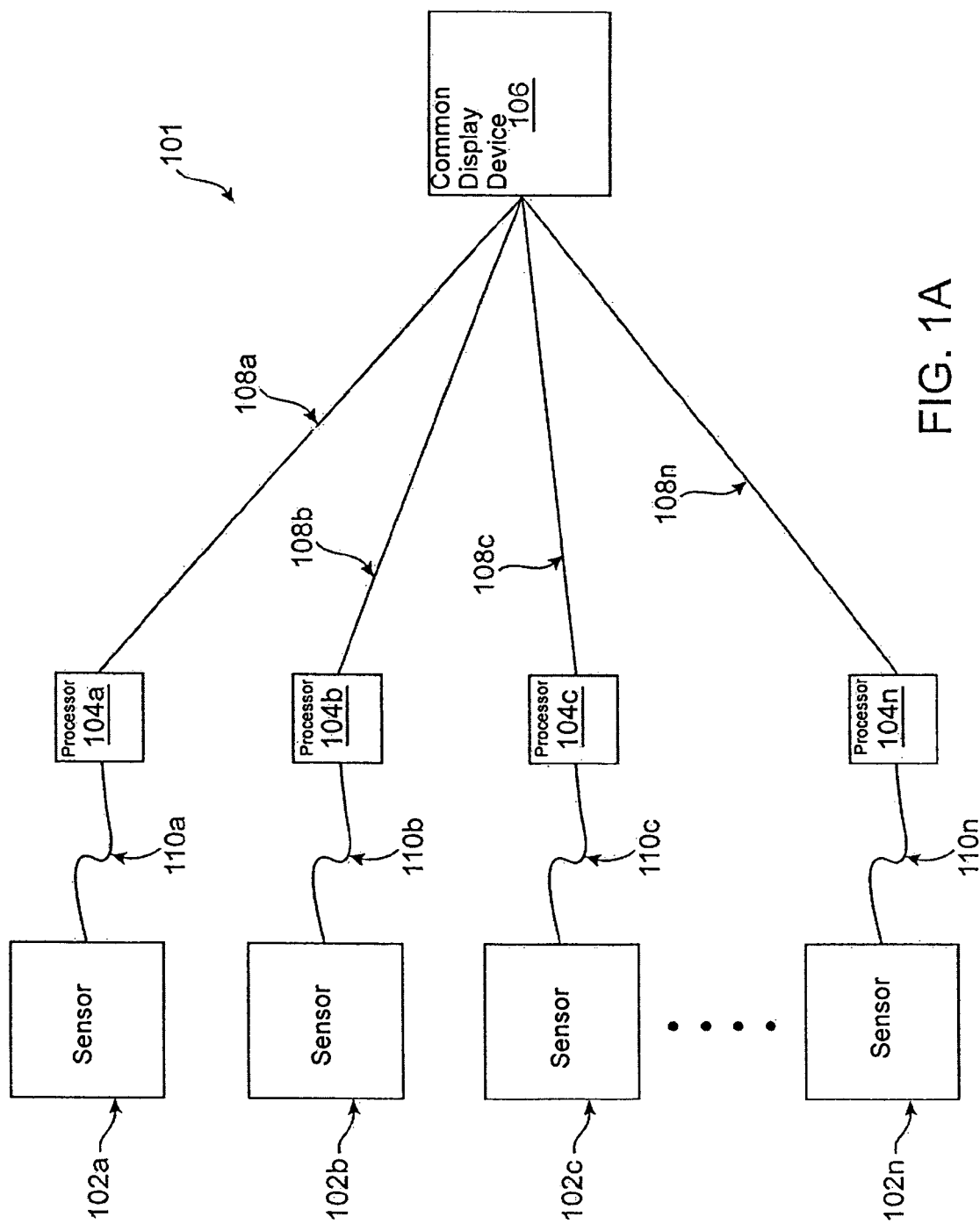
FIG. 1A is a schematic diagram of a system for passive monitoring of multiple patients according to an embodiment of the present invention.

With reference now to FIG. 1A, a multi-patient monitoring system 101 suitably includes any number of sensor devices 102*a-n*, any number of processors 104*a-n*, a common display device 106 such as an alarm, monitor or the like and any number of connectors 110*a-n*, 108*a-n*. In other embodiments, multiple sensor devices 102*a-n* may be coupled with a common processor and that processor, in turn, may be coupled with display device 106. In still other embodiments, one or multiple processors may transmit data to multiple display devices, such as to multiple digital pagers, digital handheld devices, multiple monitors or the like, as show in FIG. 1D. Any combination of sensor devices 102*a-n*, processors 104*a-n*, connectors 108*a-n*, 110*a-n* and display devices 106 is contemplated within the scope of the invention.

Figure 1B:
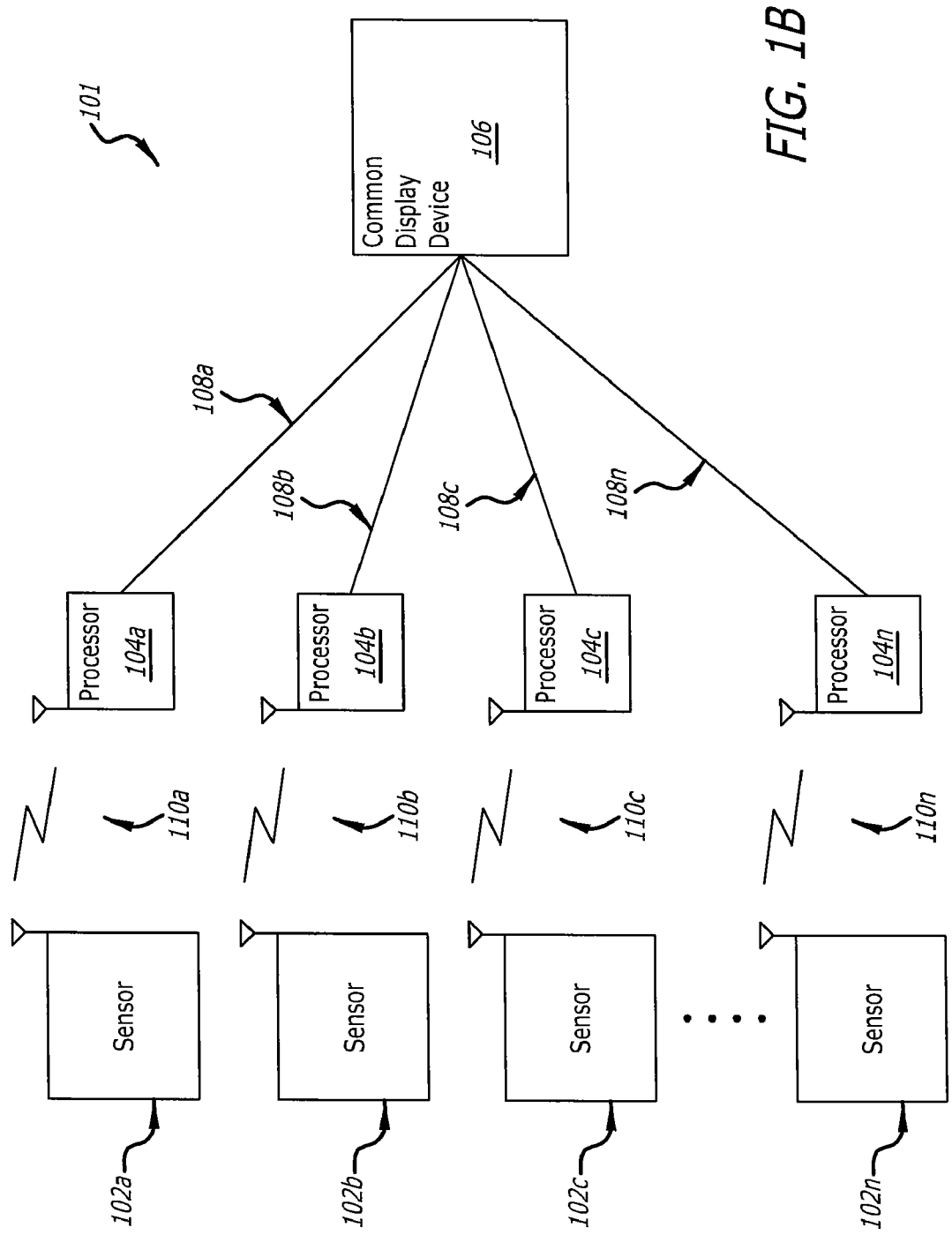
FIG. 1B is a schematic diagram of a system for passive monitoring of multiple patients according to yet another embodiment of the present invention.
Figure 1C:
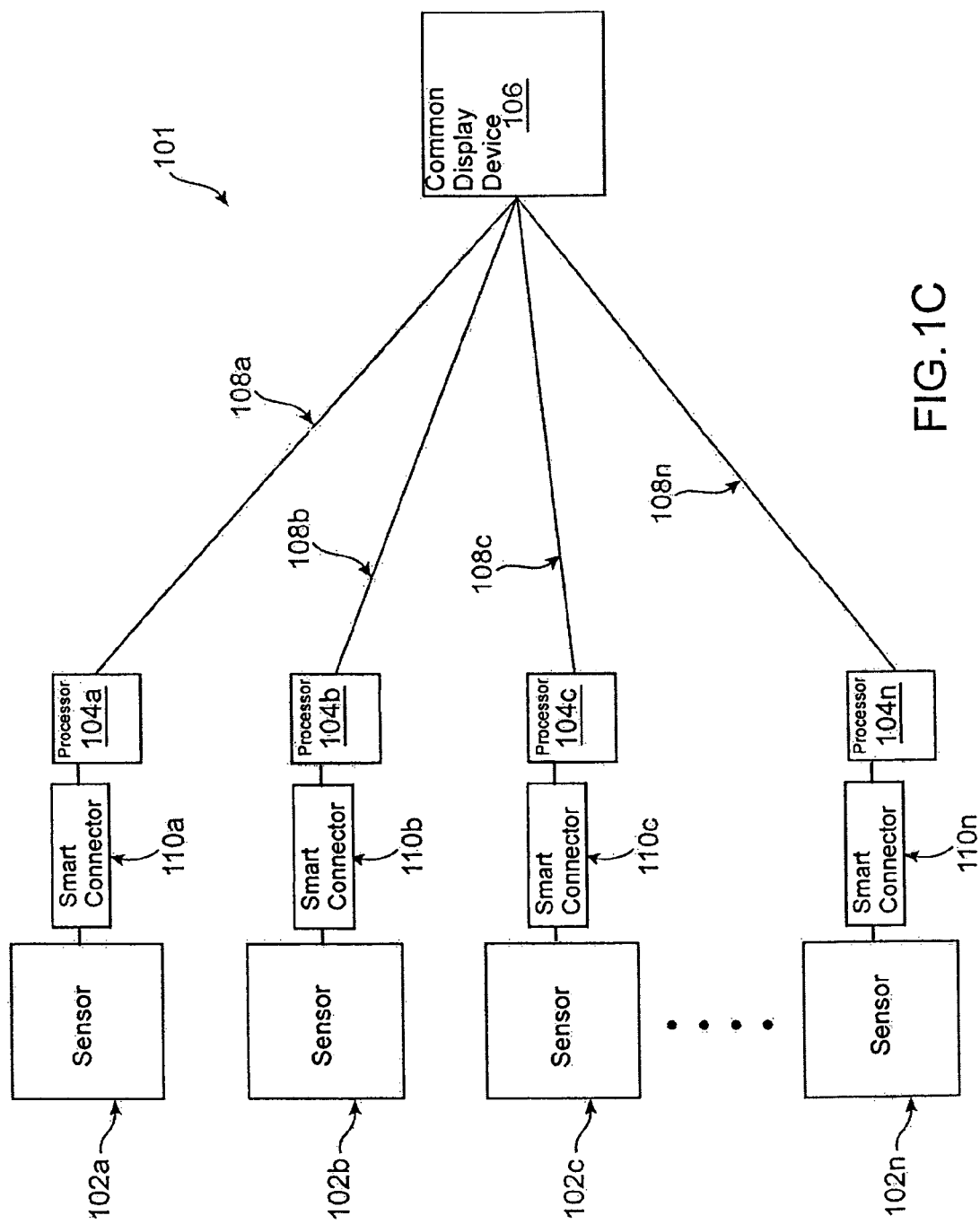
FIG. 1C is a schematic diagram of a system for passive monitoring of multiple patients according to still another embodiment of the present invention.
Figure 1D:
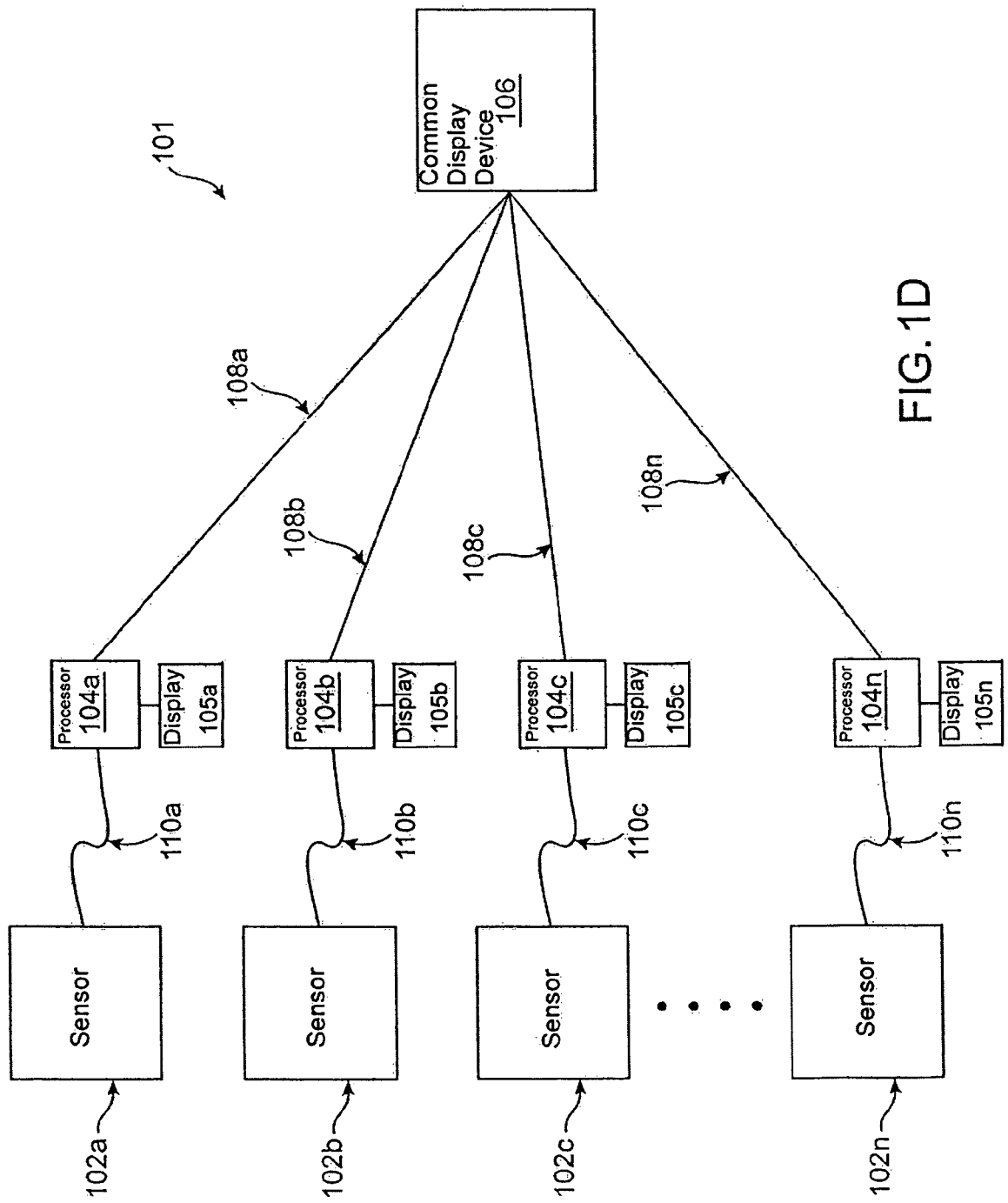
FIG. 1D is a schematic diagram of a system for passive monitoring of multiple patients according to yet another embodiment of the present invention.

Connectors 108*a-n*, 110*a-n* may comprise any suitable means for coupling sensor devices 102*a-n* with processors 104*a-n* and for coupling processors 104*a-n* with display device 106. In some embodiments, for example, connectors comprise wired connection means, while in other embodiments one or more connectors are wireless. For example, as shown in FIG. 1B, connectors 110*a-n* between sensor devices 102*a-n* and processors 104*a-n* may be wireless, while other connectors 108*a-n* may include wires. In one embodiment, as shown in FIG. 1C, connectors 110*a-n* include a "smart connector" device. A smart connector may comprise a microchip or any other suitable data carrying or processing means and may be used to assure compatibility between a sensor device and a processor. For example, when a sensor 102 is coupled with a processor 104 via a smart connector 110, the smart connector may be able to detect what type of sensor device 102 has been coupled with the processor 104, how many times the sensor device 102 has been used, whether the sensor device 102 is compatible with the processor 104 or the like. Such a smart connector may include a wired connection with complementary plugs or any other suitable connector. It should be understood, however, that any connection means may be used for coupling various elements of the present invention.

Figure 2:
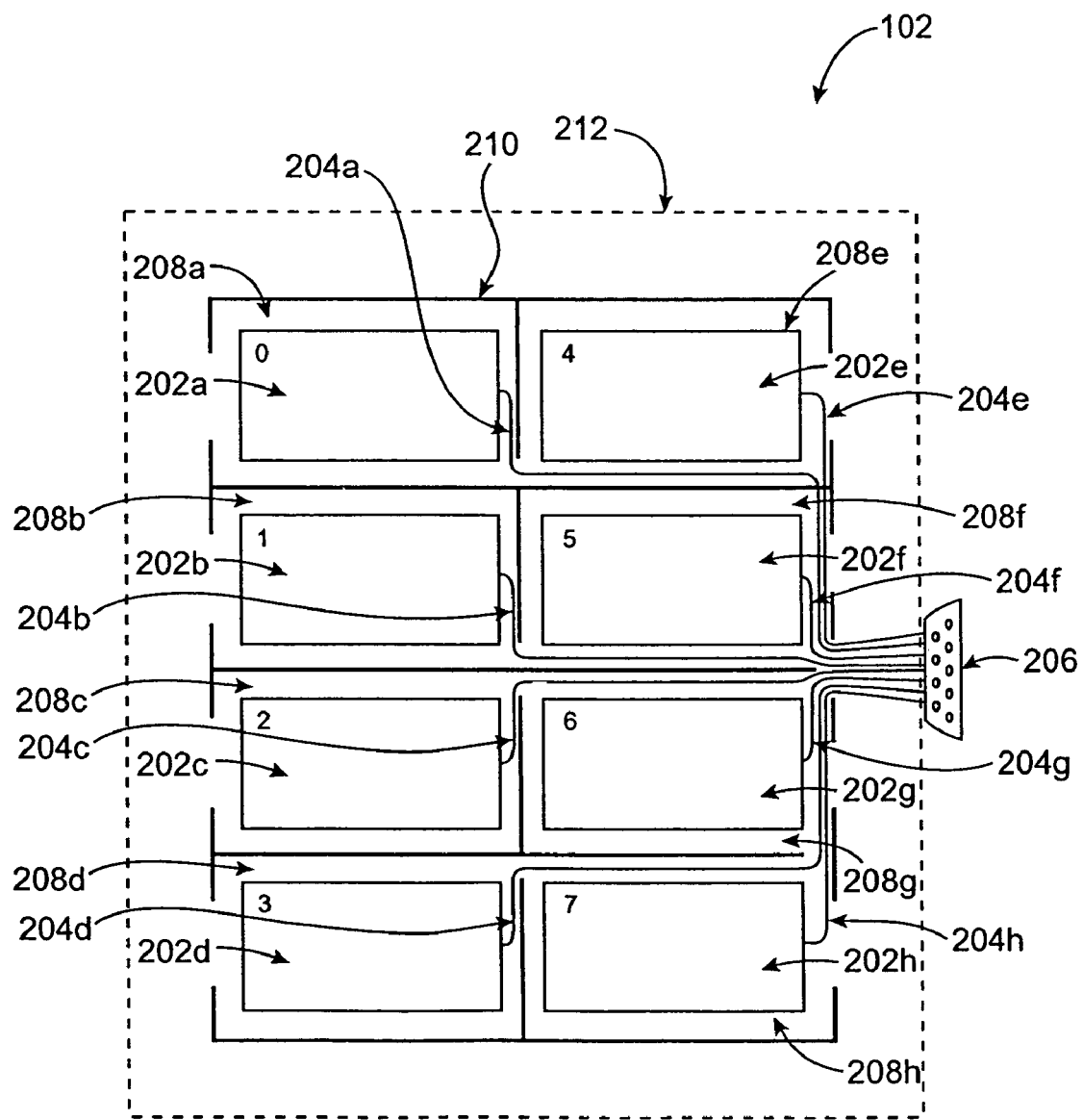
FIG. 2 is a frontal view of a sensor device, according to an embodiment of the present invention.

Referring now to FIG. 2, sensor device 102 generally includes two or more piezoelectric sensors 202 disposed along a surface 212 such that the sensors may be conveniently and passively coupled with a patient. Each sensor 202 may be of any size, shape, configuration, material or the like. Generally, each sensor 202 comprises piezoelectric material. In many embodiments, the material used is the polymer polyvinylidene fluoride (PVDF), but any piezoelectric material or combination of materials may be used, including but not limited to PVDF film, PVDF cable, piezoelectric ceramic discs and/or piezoelectric foam. Piezoelectric materials of the present invention may have any suitable shape, size and configuration. In some embodiments, for example, a thin PVDF film is used, alone or in combination with PVDF cable. In some embodiments, sensors 202 comprise rectangular, flat, thin pieces of PVDF film. In other embodiments, sensors 202 may comprise circular, triangular, square or any other shape of PVDF film, circular or any other suitable shape of flat piezo-ceramic materials, or any other suitable materials. In one embodiment, for example, each sensor 202 is paper thin or thinner and has a width of about 6 inches and a length of about 9 inches. In other embodiments, each sensor may be larger, may be only millimeters in width and length or may even be on a nanometer scale.

Referring to FIGS. 2A-F, several embodiments of sensor devices 102a-f are shown, each having a different configuration of sensors. In FIG. 2A, two, flat, rectangular PVDF film sensors 218 are included. In FIG. 2B, three PVDF film sensors 218 are used in combination with PVDF cable 220. In FIG. 2C, PVDF cable 220 is used alone in a zigzag configuration which may comprise one cable or multiple cables. In FIG. 2D, multiple piezo-ceramic discs 230 are used. In FIG. 2E, PVDF film sensors 218, 222 are used in a pattern with higher concentration of sensors 222 in one area of the device and lower concentrations of sensors 218 in other areas. Such a pattern may be advantageous, for example, in positioning higher concentrations of sensors in a position where a patient measurement is likely to be stronger, such as directly under a chest of a patient to monitor heart- and respiratory-related signals. Finally, in FIG. 2F, two piezoelectric foam sensors 240 are used. Thus, it can clearly be seen that any suitable combination and configuration of sensors may be used.

With reference again to FIG. 2, piezoelectric sensors 202 generally act as strain gauges to sense changes in stress exerted against the sensors 202. Detected stress changes may then be converted to data that is useful for patient monitoring purposes. Patient body weight exerted against one sensor 202 may be measured as stress against one sensor and compared to a similar measurement from one or more other sensors 202 on the same sensor device 102, to determine where the patient is positioned on a device, whether the patient is moving and/or the like. Expansion of a patient's lungs during inhalation or the beating of a patient's heart may exert stress against one or more piezoelectric sensors 202 positioned under or near the patient's chest. The sensors 202 sense such stress changes, and the sensed changes may be processed to determine respiratory rate, heart rate, body movement, body position and the like. Many other possible measurements, some of which are described further below, may be derived from information gathered from sensors 202. For further description of pressure-sensing capabilities of piezoelectric materials, reference may be made to U.S. patent application Ser. No. 09/662,006 entitled "Passive Physiological Monitoring Systems and Methods," filed by the inventors of the present invention n Sep. 9, 2000, the full disclosure of which is hereby incorporated by reference.

As described above, devices of the present invention generally include a surface 212 and two or more piezoelectric sensors 202. Both surface 212 and sensors 202 may have any suitable configuration. For example, in some embodiments surface 212 comprises simply one or more pieces of resilient foam material, plastic, paper or any other suitable material. In other embodiments, surface 212 comprises two layers of foam material coupled together with adhesive or by any other suitable means. Sensors 202 may be coupled with surface 212 by adhesive, by sandwiching sensors 202 between two layers of surface 212 and via adhesive, or by any other suitable means. Therefore, the following description is provided to explain one embodiment of the invention and should not be interpreted to limit the scope of the invention as set forth in the appended claims.

In some embodiments, sensor device 102 includes surface 212, which has a housing 210 with pockets 208a-h for containing piezoelectric sensors 202a-h. As shown in FIG. 2, each piezoelectric sensor 202a-h, is coupled with a sensor transmitter 204a-h, which may comprise an electrical lead or wire, as shown, or alternatively a wireless transmitter or the like. Finally, in some embodiments multiple sensor transmitters 204 may be coupled with a sensor transmitter connector 206. Sensor transmitter connector 206 generally acts as a common connector for coupling the piezoelectric transmitters 204a-h with processor 104. In other embodiments, any other suitable means for coupling piezoelectric sensors with processor 104 is contemplated. Such coupling may comprise wireless connection via radio frequency, microwave, infrared or any other suitable wireless transmission means, may involve multiple wires, may involve a common wire originating from a location within surface 212 at which the separate transmitters 204a-h are connected, or the like.

Any suitable size, shape, thickness and overall configuration of surface 212, housing 210, pockets 208a-h and sensors 202a-h may be used. For example, some embodiments have only two piezoelectric sensors 202 with two accompanying pockets 208, while others have four, eight (as in FIG. 2), sixteen, thirty-two or any other suitable number of sensors 202 and pockets 208. One arrangement of sensor 202 on surface 212 may be referred to as "an array" or "a passive sensor array (PSA)". Such a PSA generally comprises a grid-like pattern of sensors 202 on surface. Such a grid may comprise rectangular PVDF film sensors 202, as shown in FIG. 2, or any other shapes, sizes or types of sensors, as demonstrated in FIGS. 2A-2F. The PSA may include any suitable number of rows and columns of sensors 202 and certain patterns may have advantages in certain settings. It may be desired, for example, to have only two sensors 202 on surface 212 in an embodiment of sensor device 102 configured for use on a chair seat or chair back. In another embodiment, it may be advantageous to have two columns, each column having four sensors, perhaps for use in a sensor device 102 configured for a baby's crib. In yet another embodiment, three columns of eight sensors 202 each may be used for a hospital bed configuration. Any number of rows, columns and sensors 202 may be used in any given embodiment. In some embodiments, it may be advantageous to use PVDF cable, by itself or in conjunction with PVDF film. For example, in one embodiment PVDF cable may be used around a perimeter of surface 212 for detecting patient movement on an edge of a bed.

In one embodiment, each sensor 202 is contained in a separate pocket 208, but other configurations and combinations are contemplated. For example, sensors 202 may be simply sandwiched between two layers of surface 212 and may be coupled with surface 212 via adhesive. Housing 210 may include multiple pockets 208a-h or sleeves, each for housing one sensor 202, or may include one or more larger pockets for housing multiple sensors 202. Although any sizes may be used, in one embodiment as in FIG. 2, eight sensors are disposed along a surface having dimensions of about 32 inches by 24 inches. In such an embodiment, each sensor may have dimensions of about 9 inches by 6 inches. It should be emphasized that any configuration, pattern, dimension and the like of sensors 202 and surface 212 is contemplated within the scope of the invention.

Surface 212, housing 210 and pockets 208a-h may be comprised of any suitable material or combination of materials, such as but not limited to neoprene, plastics, polypropylene, natural or manmade fibers, Poron, Scappa, PVC, foam, Tyvek and the like. In one embodiment, surface 212, housing 210 and pockets 208a-h comprise a resilient foam material such as neoprene. For example, one layer of neoprene may be used as surface 212 and an additional layer may be used to form pockets 202a-h. In another embodiment, two layers of neoprene are sandwiched together, with sensors in between, and adhesive is used to couple the layers together and to couple the sensors to the neoprene. Such a neoprene surface 212 and housing 210 may comprise a flat device resembling a pad, and in some embodiments the neoprene material may provide pad-like comfort when sensor device 102 is positioned under a patient on a bed, chair or the like. In some embodiments, surface 212 may also include extra padding, of neoprene or any other suitable material, to enhance comfort of a patient lying or otherwise applying weight against surface 212. Thus, surface 212 may sometimes generally be referred to as a "pad" or "sensor pad."

Pockets 208a-h may be given any suitable shape to hold or contain sensors 202a-h. Some pockets 208, as shown in FIG. 2, may be configured as a layer of neoprene or other material attached to surface 212 and having an opening for allowing a sensor 202 to be placed within a pocket 208. Openings may also allow sensor transmitters 204 such as wires, flex connectors or the like to pass through housing 210 to be coupled with sensor transmitter connector 206. In some cases, as in FIG. 2, each pocket 208 may have one opening for allowing passage of a sensor 202 and one opening for allowing passage of a sensor transmitter 204. In one embodiment, the width of an opening is less than the width of sensor 202, so that sensor 202 may be bent or folded to fit within a pocket 208 and then allowed to flatten within the pocket 208, so that generally sensor 202 will remain in place within pocket 208. Openings may allow sensors 202 to be reused while disposing of surface 212, in some embodiments. Alternatively, and more preferably, openings are used to place sensors 202 in pockets 208 during fabrication but are permanently sealed after sensor 202 placement. In other embodiments, no openings are included. Any other suitable configuration of pockets 208 may be used.

In some embodiments, multiple sensor transmitters 204 may be connected to or coupled with one or more sensor transmitter connectors 206. Sensor transmitter connector 206 may be located anywhere on or around surface 212 and will generally provide for more convenient coupling of sensor transmitters 204 to processor 104 or other device. Any other suitable means for coupling one or more sensor transmitters 204 to a processor may alternatively be used.

Referring now to FIG. 3A, a sensor 202 is shown separately with a sensor transmitter 204. As shown in FIG. 3B, two or more sensors 202a-b and transmitters 204a-b may be coupled with a surface 212 having a housing 210 with two or more pockets 208a-b. With reference to FIG. 3C, some embodiments of sensor device 102 further include a sheath 302 for covering or containing all or a portion of surface 212 and sensors 202. Sheath 302 may have any suitable configuration and size and may include any suitable material or combination of materials. In one embodiment, for example, sheath 302 comprises an envelope-like structure having a first side 302a and a second side 302b. In one embodiment, such an sheath 302 may open and close (curved arrow) via a connection along one edge, to allow surface 212 and sensors 202 to be placed inside sheath 302. Another embodiment may include a similar sheath 302 with two layers or sides 302a-b that are connected along two or three edges, to create a pocket or sleeve into which surface 212 and sensors 202 may be placed.

Although any suitable material or combination of materials may be used in manufacturing sheath 302, one typical embodiment uses materials having some degree of water resistance. For example, sheath may be made of a foam material, plastic, paper, nylon, PVC, fibrous material, any combination thereof, or any other suitable material or combination of materials. In many patient care settings, it may be advantageous to have a water resistant sheath 302 to protect surface 212 and sensors 202 from urine, water, blood, or any other liquids that may be spilled on a patient bed or chair and which may cause damage to an unprotected surface 212 or sensor 202. Thus, sheath 302 generally protects surface 212 and sensors 202, to allow them to be reused for multiple patients and to increase their usable lives. Some surfaces 212 and sensors 202, for example, may be used for up to six months or more. On the other hand, in some embodiments sheath 302 may be disposable and used for only one patient, for only one day, or the like.

To assure proper use and/or to prevent reuse of sheath 302, some embodiments of sheath 302 and surface 212 include complementary connectors 310 and 312 as shown in FIG. 3C for creating a connection between sheath 302 and surface 212. Such a connector may be any suitable coupling mechanism, such as an electronic coupling means, a circuit which is completed through the connection of complementary parts, or the like, and will typically be configured to enable sensor device 102. Thus, in some embodiments, it may be required, before using sensor device 102 to monitor a patient, to couple surface 212 with sheath 302. Sheath 302 may activate or allow device 102 to operate to monitor the patient. This coupling/enabling requirement may prevent reuse of sheath 302 between patients, which may help prevent spread of infections between patients, prevent misuse of sensor device 102 and enhance the usable life of sensor device 102.

As previously explained, surface 212, housing 210, sensors 202 and the like may have any suitable size, shape and configuration. In one embodiment, for example, as shown in FIGS. 3B and 3C, surface may have a length of about 16 inches and a width of about 12 inches. Housing 210 may have a width 304 of about 10 inches and a length of about 14 inches. One pocket 208a or 208b may have a length 304 of about 10 inches and a width 306 of about 7 inches. In such a configuration, one sensor 202a or 202b may have dimensions of about 6 inches by about 9 inches. These are only exemplary dimensions, however, and any suitable dimensions for surface 212, sensors 202, housing 210, pockets 208 and the like are contemplated.

Referring again to FIG. 1, sensor device 102 may generally be coupled with processor 104. Processor 104 includes any suitable means for receiving mechanical signals, sensed by piezoelectric sensors 202 of sensor device 102 (or any other suitable sensor device) and processing those signals to provide patient data to one or more users. In some embodiments, processor 104 comprises a bed-side unit, couplable with sensor device 102 via one or more wired connections, wireless connections or the like. In other embodiments, processor may comprise a circuit board, a computer chip, a software program and/or any other suitable processing means. Thus, processor 104 in some embodiments comprises a stand-alone device, which may couple with sensor 102 to process signals and provide data to a user, while in other embodiments processor 104 comprises an add-on device which may be used in conjunction with hardware provided separately, for example by an original equipment manufacturer.

Figure 4:
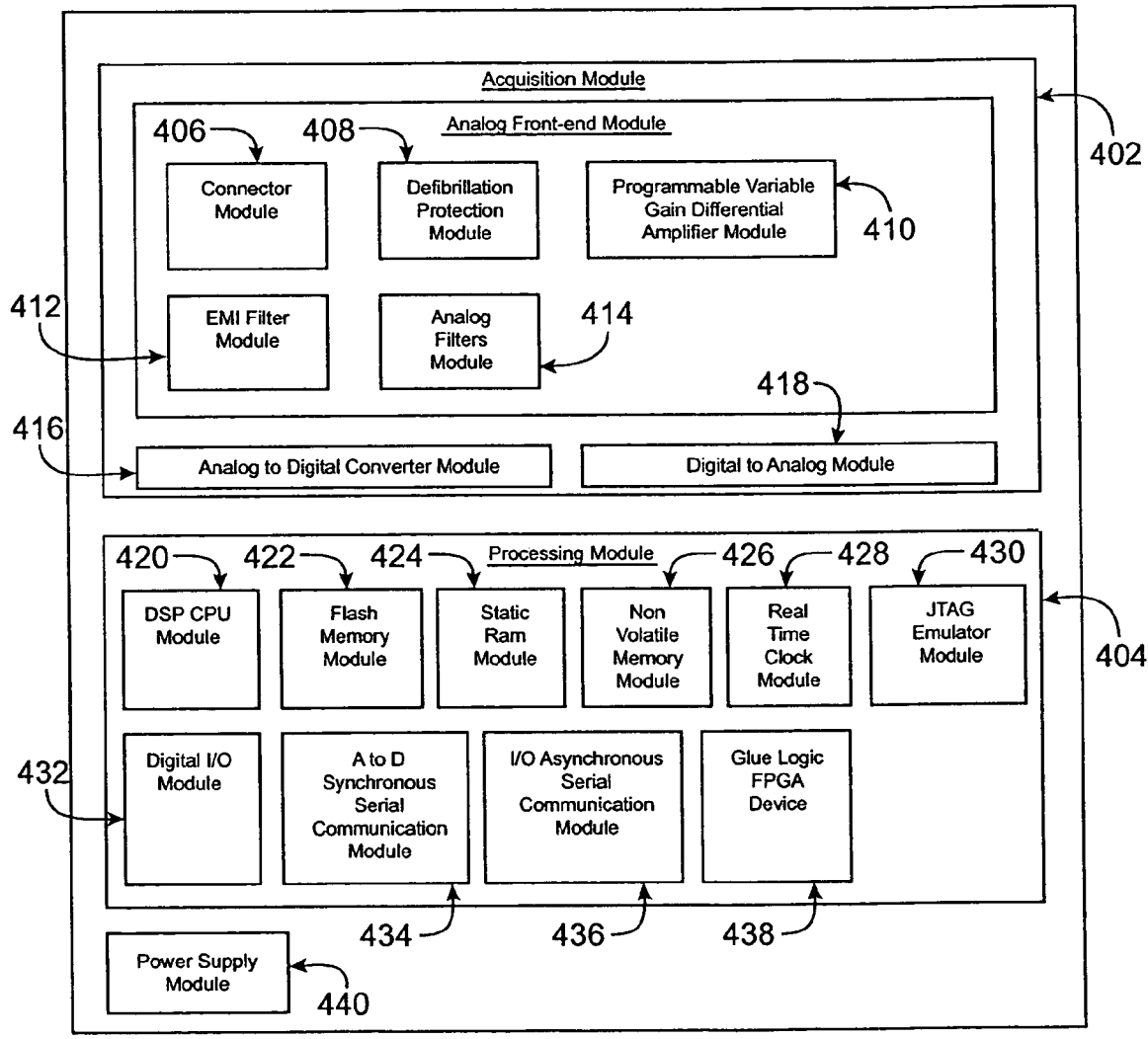
FIG. 4 is a block diagram showing elements of a processor for processing signals, according to an embodiment of the present invention.

With reference now to FIG. 4, an embodiment of an add-on processor 104, for use with hardware such as a bedside monitoring unit or any other suitable hardware is shown. Generally, processor 104 includes any suitable means for processing mechanical signals into usable patient data. For further description of signal processing devices and methods, reference may be made to U.S. patent application Ser. No. 09/662,006, previously incorporated herein by reference. In some embodiments, processor 104 suitably includes an acquisition module 402 coupled with a processing module 404 and a power supply 440. Acquisition module may include a connector module 406, a defibrillation protection module 408, a programmable variable gain differential amplifier module 410, and EMI filter module 412, an analog filters module 414, an analog to digital (AD) converter module 416, and a digital to analog converter module 418. It should be emphasized that acquisition module 402 in various embodiments may include fewer components or additional components and/or that various modules may be combined to create fewer modules. Generally, acquisition module 402 acquires analog mechanical signals from sensor device 102, filters those signals with one or more filtering means and converts the filtered signals to digital signals. Any means for acquiring, filtering and converting may be used.

Processor 104 may also include processing module 404. Processing module 404 may include a digital signal processor/central processing unit (DSP/CPU) module 420, a flash memory module 422, a static RAM module 424, a non-volatile memory module 426, a real time clock module 428, a joint test action group (JTAG) emulator module 430, a digital input/output module 432, an AD synchronous serial communication module 434, an input/output asynchronous serial communication module 436 and a glue logic field programmable gate array (FPGA) device 438. Again, various modules may be combined, eliminated or added without departing from the scope of the present invention.

Power supply 440 is coupled with acquisition module 402 and processing module 404 in some embodiments to provide a source of energy for processor 104. Power supply 440 may comprise any suitable energy supply, such as a battery, a connection to an external power supply and/or the like. In some embodiments, power supply 440 is not included. For example, in some embodiments acquisition module 402 and processing module 404 may be provided for use with existing hardware, and the hardware may already include a power supply. This would be the case, for example, in embodiments in which acquisition module 402 and/or processing module 404 were provided in the form of one or more circuit boards, chips or the like to be added to a computer, bedside monitor or other patient monitoring device. Thus, it should again be emphasized that processor 104 shown and described in FIG. 4 is one exemplary embodiment only, and should not be interpreted to limit the scope of the invention in any way.

As mentioned briefly above, processor 104 generally receives one or more mechanical signals from sensor device 102 and processes the signals to provide patient data to a user. For example, processor may receive mechanical signals in the form of pressure change signals from sensor device 102. Such signals are generally received by processor via a multi-channel circuit, each channel corresponding to one piezoelectric sensor 202 of sensor device 102. Filtering means, such as EMI filter module 412, analog filters module 414, filtering software, processing software, smart algorithms and/or the like then filters the signals, for example to remove background noise and the like. Signals are then converted into digital signals by AD converter module 416. Digital signals may then be processed by various means. In some embodiments, as described further in U.S. patent application Ser. No. 09/662,006, fast Fourier transform (FFT) methods may be used. In other embodiments, time-domain analysis may be used. Still other embodiments may use a combination of the two methods. At some point during the processing of signals, at least one type of signal is compared between multiple piezoelectric sensors 202 of sensor device 102. For example, mechanical pressure change signals may be compared between multiple sensors 202 on a sensor device 102. The comparison of signals, may allow processor 104 to provide a user with patient data such as where a patient is positioned on sensor device 102, whether the patient is moving on sensor device 102, whether the patient is present on the sensor device 102, whether all patient motion has stopped or has gone below a predetermined level, and/or the like.

In some embodiments, signals may be compared to allow processor 104 to select a signal with the best fidelity, information content or the like. For example, signals may be compared and the signal relating to respiration may be selected from a sensor 202 having the highest quality respiration signal. Similarly, the highest fidelity heart beat signal may be chosen from a sensor 202 that is sensing the highest fidelity heart beat signal. It may be possible as well for one sensor 202 to sense a highest quality respiratory signal and a highest quality heart beat signal (or any two or more types of signals) at the same time and provide those signals as data to a user. Comparison between sensors 202 may also allow processor to determine what portion of a mechanical signal relates to a given physiological parameter. For example, comparison of a mechanical signal from a first sensor 202 located under a patient's chest will typically have a stronger respiratory component than a mechanical signal from a second sensor 202 located under the patient's left foot. These signals may be compared to segregate or define a respiratory signal. Again, such methods for processing signals, any of which may suitably be used by processor 104, are described more fully in U.S. patent application Ser. No. 09/662,006, previously incorporated by reference.

In addition to filtering signals and comparing signals between sensors 202, processor 104 may process mechanical, analog signals received from sensor device 102 in any suitable way. For example, in some embodiments processor 104 compares a given signal or signals to one or more threshold levels and provides data to activate an alarm if the given signal is above or below a threshold. For example, thresholds of minimum and maximum amounts of patient movement in a hospital bed, of minimum and maximum respiratory rates, of minimum and maximum heart rates and/or the like may be stored in processor 104. If signals sensed from a patient fall outside one or more of the thresholds, processor 104 may provide data to a user in the form of an alarm activation signal. In some embodiments, combinations of thresholds may be set. For example, a minimum heart rate threshold may be defined such that it will only cause alarm activation if both the patient's respiratory rate falls below the threshold and the patient's heart rate falls below a heart rate threshold. Any combination of such thresholds, alarm activation processing and the like are contemplated. Furthermore, one or more thresholds may alternatively be fixed by a manufacturer of processor 104, such that the thresholds are "hard wired" for all patients, or may be adjustable by a nurse, physician or other user for each individual patient, for a general care floor of a hospital or the like.

Still further functions of processor 104 may include processing signals to provide respiratory rate and/or heart rate data. Such data may be provided as respirations per minute, heart beats per minute, wave signal data showing a line or wave representing respirations, heart beat and/or the like, or any other suitable form. Patient motion or position may also be provided in any suitable form, such as an amount of motion, a location of motion, a patient position mapped on a hospital bed or chair, or the like. As has been mentioned previously, other parameters may also be measured and provided, such as blood pressure, cardiac output, blood volume, respiratory tidal volume, body temperature and temperature change, and/or the like.

Again referring to FIG. 1, once sensor device 102 has sensed one or more signals from a patient and processor 104 has processed those signals to provide patient data, the data is typically provided to a user in some usable form. In many embodiments, processor 104 simply provides the data to a pre-existing system of the user. In one embodiment, for example, processor 104 is coupled with an intranet or the Internet via an Ethernet connection. A user may then access data via any computer or other device having intranet or Internet access. In various embodiments, processor 104 may also provide for storage, display and/or downloading of data at preset intervals, such as every 30 seconds, every minute or the like, over a period of several days, several weeks or any other period. Stored data may be downloaded to a computer, monitor, printer, portable data storage device or any other suitable hardware or software location. In another embodiment, processor 104 provides data in the form of an alarm activation of a pre-existing alarm system, such as a hospital's nurse call system. Such a system may be located at bedside, outside each hospital room, at a common nurse call station and/or the like. In still other embodiments, data may be provided via one or more digital pager or wireless handheld devices via wireless transmission.

Processor 104 may include any suitable connector 108 for coupling processor 104 with a means for accessing data by a user. For example, connector 108 may comprise a wired connection, a wireless connection, a connection to a computer network, an electrical connection to an alarm system or any other suitable connection. Thus, although system 100 in FIG. 1 includes display device 106, it should be understood that systems, devices and methods of the present invention may suitably include sensor device 102 and processor device 104 and may provide data to one or more pre-existing display device, alarm, pager or other systems.

In other embodiments, display device 106 may be provided, either housed in a separate device or in the same device in which processor 104 is housed. For example, a bedside box-like unit coupled to a sensor device 102 may include processor 104 and display device 106 including an alarm and a screen for viewing physiological data. Alternatively, in other embodiments processor 104 and display device 106 may be separate pieces. For example, processor 104 may be a bedside unit and may transmit physiological data to one or more central and/or remote display devices 106. As discussed briefly above, display device 106 may include one or more devices for providing physiological data pertaining to one or more patients to a user. In one embodiment, display device 106 comprises a bedside alarm which sounds when a patient reaches a predefined physiological threshold. In another embodiment, display device 106 comprises an alarm and a display monitor or screen for viewing physiological data pertaining to one or multiple patients.

Display device 106 may be located at any suitable location. For example, some display devices 106 are positioned at a patient's bedside or in a patient's room. In other embodiments, display device is located at a common location, such as at a nursing station or central monitoring station on a hospital floor, in a hospital ward, or the like.

In yet another embodiment, display device 106 may comprise one or a plurality of mobile, wireless devices, such as digital pagers or wireless handheld devices, which may allow a nurse, physician or other user to receive patient physiological data remotely. In still other embodiments, patient data may be available on a personal computer, handheld device or the like via a secure connection to the Internet. Thus, any form, number or combination of display devices 106 are contemplated within the scope of the present invention.

Figure 5:
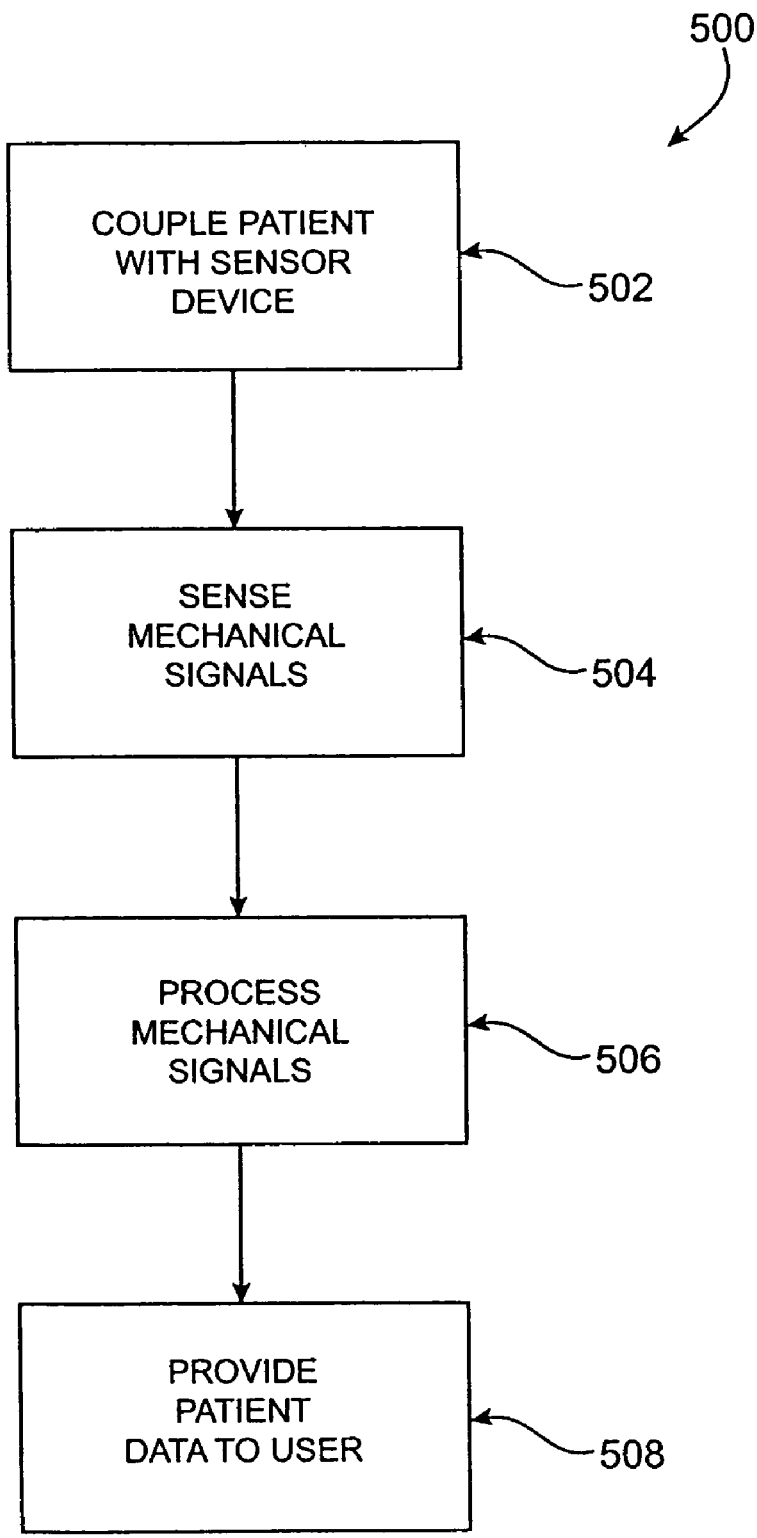
FIG. 5 is a flow diagram showing a method for passively monitoring a patient, according to an embodiment of the present invention.
Figure 6:
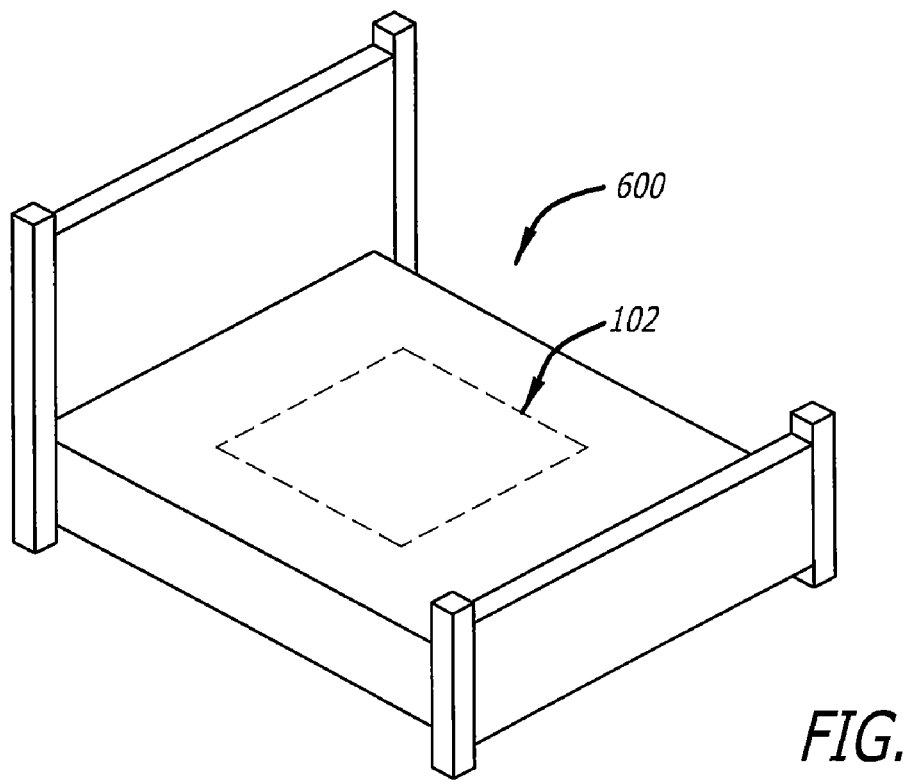
FIG. 6 is a schematic perspective view of a bed provided with a sensor device according to one embodiment of the present invention.
Figure 7:
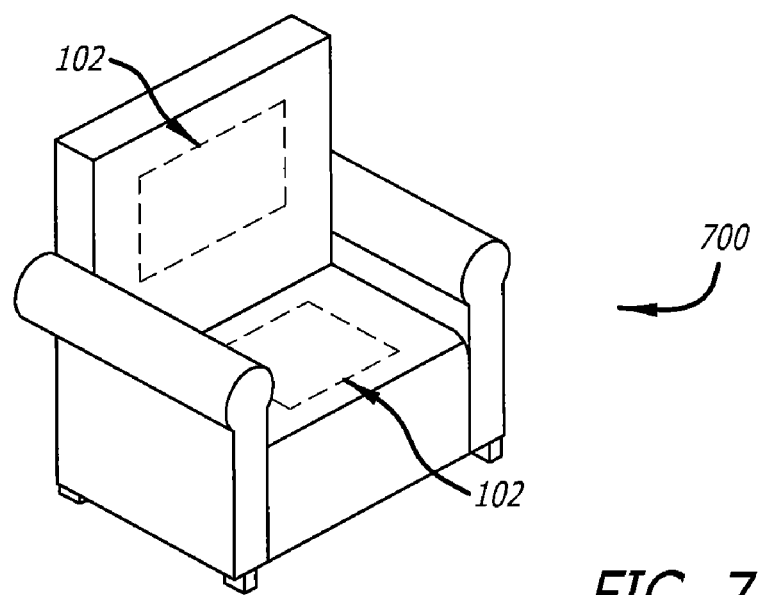
FIG. 7 is a schematic perspective view of a chair provided with a sensor device according to another embodiment of the present invention.
Figure 8:
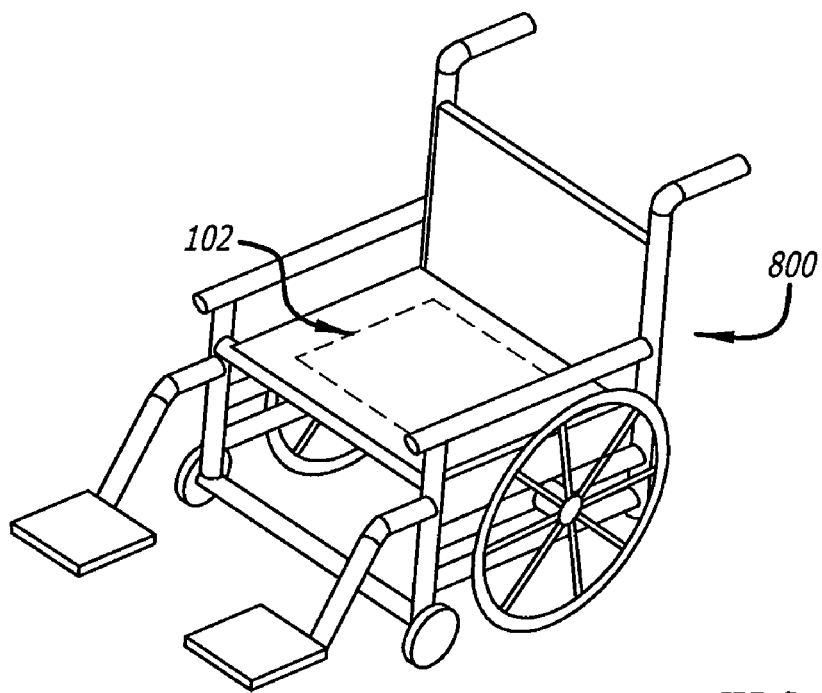
FIG. 8 is a schematic perspective view of a wheelchair provided with a sensor device according to yet another embodiment of the present invention.
Figure 9:
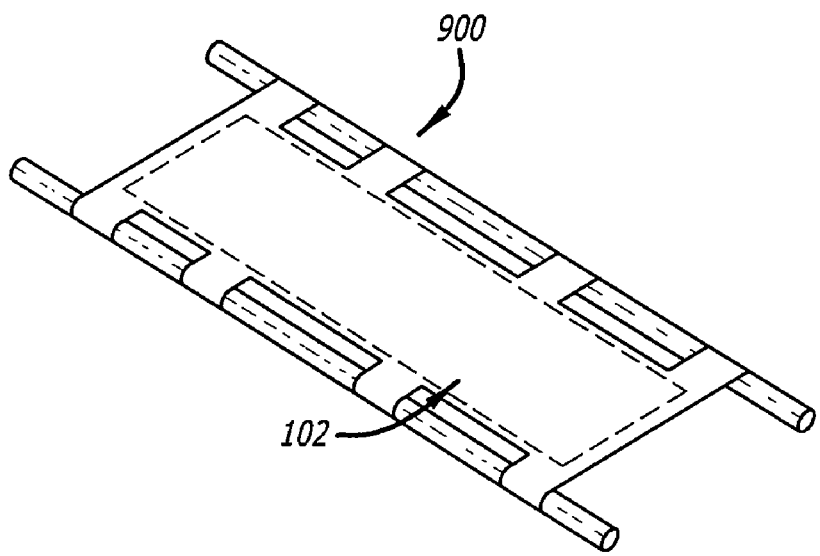
FIG. 9 is a schematic perspective view of a stretcher provided with a sensor device according to still another embodiment of the present invention.
Figure 10:
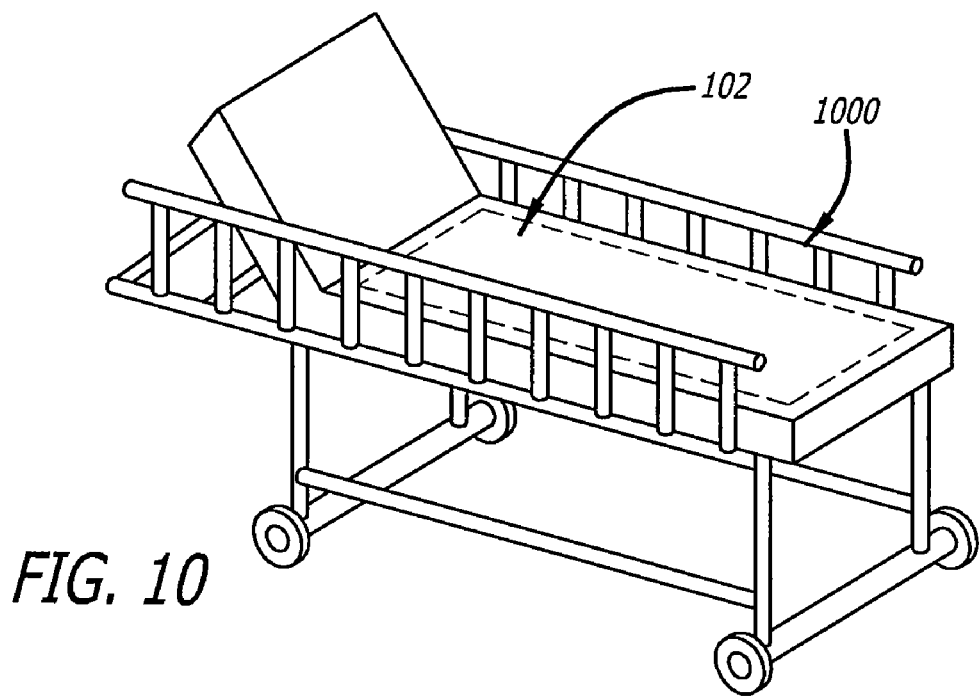
FIG. 10 is a schematic perspective view of a gurney provided with a sensor device according to yet another embodiment of the present invention.
Figure 11:
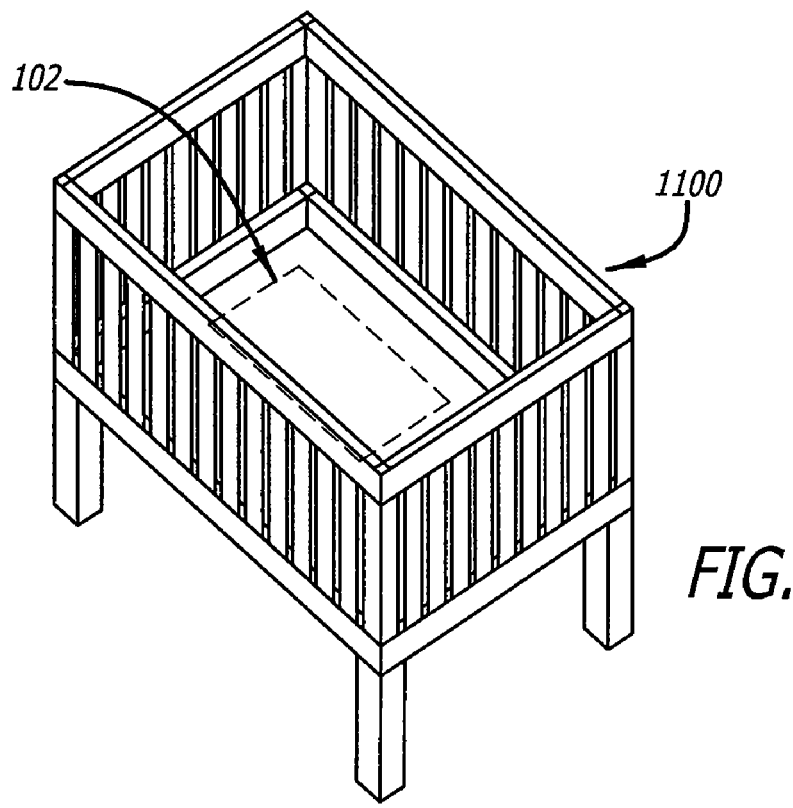
FIG. 11 is a schematic perspective view of a crib provided with a sensor device according to yet another embodiment of the present invention.

With reference now to FIG. 5, a method 500 according to one embodiment of the invention suitably includes coupling a patient with a sensor device 502, sensing at least one mechanical signal of the patient 504, processing the mechanical signal into patient data 506 and providing the patient data to a user 508. Generally, before coupling a patient with the sensor device 502, sensor device 102 is provided on a surface. As described above, the surface may include any suitable surface, such as but not limited to a hospital bed, a conventional bed 600 (FIG. 6), an operating room table, an examining table in a doctor's office, a procedure chair or table for performing a procedure under conscious sedation, a dentist's chair, a hospital chair or other chair 700, in a chair seat and/or chair back (FIG. 7), a wheelchair 800 (FIG. 8), a baby's crib 1100 (FIG. 11), a stretcher 900 (FIG. 9), or gurney 1000 (FIG. 10) or the like. In other embodiments, the surface may be wearable, in the form of a gown, sleeveless jacket, strap or the like. Providing sensor device 102 on the surface may comprise simply placing sensor device 102 on the surface or may involve integrating sensor device 102 into the surface. For example, sensor device 102 may be built into a hospital bed surface or a chair seat or back. In some embodiments, sensor device 102 may be provided under one or more layers of material, such as when a sensor device is placed under one or more sheets on a bed, is placed within an envelope- or duvet-like cover on a bed, is placed below a cushion on a seat or the like. Thus, sensor device 102 may be provided on any suitable surface by any suitable means, without departing from the scope of the invention.

Coupling the patient with the sensor device 502 generally involved allowing the patient to lie, sit, lean or otherwise apply weight or pressure against the surface on which sensor device 102 has been provided. Such lying, sitting, leaning or the like comprises an element of "passive monitoring," since the patient may not even realize that the sensor device 102 is present and since it is not required to attach sensor device 102 to patient. This is in direct contrast to currently available devices such as blood pressure cuffs, pulse-oximetry sensors, nasal canulas, ECGs and the like, all of which require active, direct attachment of one or more devices to a patient.

Sensing mechanical signals 504 generally comprises sensing at least one mechanical signal with at least one piezoelectric sensor of the sensor device 102. Generally, a sensed signal may include a pressure signal, a temperature signal, an acoustic signal or any other suitable mechanical signal. Sensors 202 typically sense changes in any given mechanical parameter, but may sense absolute mechanical signals in some embodiments. Signals sensed by sensors 202 may include either positive signals or the absence of a signal. For example, if a positive pressure-change signal is detected in one sensor 202 of sensor device 102 and no pressure-change signal is detected in another sensor 202 of sensor device 102, it may signify that the patient is positioned over the former and not the latter sensor 202, that respirations or heart rate of the patient are being sensed over the formed and not the latter sensor 202, and/or the like. Thus, in some embodiments a first sensor may sense at least one mechanical signal, a second sensor may sense at least one mechanical signal, and the sensed signals may be compared. If the first sensor, the second sensor or both actually sense no signal, than this lack of signal may be compared between sensors to provide data to a user.

Processing mechanical signals 506 has been described in detail above. Generally, such processing 506 involves at least converting mechanical signals to digital signals and comparing signals between at least two piezoelectric sensors 202 of sensor device 102. Processing 506 also involves processing mechanical signals into data which may be provided to a user. Providing patient data to a user 508 has also been described above. Data may be provided in the form of an alarm activation based on threshold criteria such as patient motion, respiratory rate and/or heart rate criteria. Data may also be provided as quantitative or qualitative patient motion or positioning data, respiratory rate data, heart rate or the like.

While the present invention has been fully described above in relation to various exemplary embodiments, it should be understood that the description of embodiments is provided for exemplary purposes only and should not be interpreted to limit the scope of the invention as described in the appended claims. Additions or modifications to any of the embodiments described and additional embodiments are contemplated within the scope of the present invention.

What is claimed is:

1. A system for passively monitoring multiple patients, the system comprising:
    a plurality of sensor devices, each sensor device comprising:
        a surface for coupling with a patient; and
        at least two piezoelectric sensors coupled with the surface for sensing at least one mechanical signal from the patient, each of the sensors comprising a piezoelectric film;
    a plurality of processors, each processor coupled with one sensor device and being operative for converting the at least one mechanical signal into at least one digital signal and for analyzing the digital signals corresponding to each of the at least two piezoelectric sensors to select the sensors with the highest quality heart rate and respiration rate signals to use for deriving heart rate and respiration rate data pertaining to the patient; and
    at least one connector coupled with each processor for connecting each processor with a common alarm system for providing an alarm based on heart rate and/or respiration rate criteria for each of the multiple patients to a user at a remote location.

2. A system as in claim 1, wherein each surface comprises a flat pad.

3. A system as in claim 2, wherein the flat pad comprises at least one layer of a resilient foam material.

4. A system as in claim 1, wherein the piezoelectric sensors are disposed along each surface in a pattern to facilitate monitoring of at least one of patient body position, patient movement, patient respiratory rate and patient heart rate.

5. A system as in claim 4, wherein the pattern comprises two or more adjacent, flat piezoelectric sensors.

6. A system as in claim 5, wherein the pattern comprises a grid pattern comprising at least two adjacent rows and at least two columns of piezoelectric sensors.

7. A system as in claim 1, wherein dimensions of each surface allow the surface to be positioned on at least one of a crib and a bed for monitoring an infant.

8. A system as in claim 1, wherein dimensions of each surface allow the surface to be positioned on a bed for monitoring a patient in a hospital, long-term care facility or nursing home.

9. A system as in claim 1, wherein dimensions of each surface allow the surface to be positioned on a chair for monitoring a patient undergoing a procedure under conscious sedation.

10. A system as in claim 1, wherein each sensor device further includes a sheath for containing at least a portion of the surface to provide a protective layer between the surface and the patient.

11. A system as in claim 10, wherein the sheath is water resistant.

12. A system as in claim 10, wherein the sheath is removable from the sensor device after being used to monitor one patient.

13. A system as in claim 1, wherein the piezoelectric sensors are selected from the group consisting of polyvinylidene fluoride film, polyvinylidene fluoride cable, piezoelectric ceramic discs and piezoelectric foam.

14. A system as in claim 1, wherein each surface is provided on a flat surface of a bed, and wherein the at least one mechanical signal of the patient may be monitored when the patient lies on the surface.

15. A system as in claim 1, wherein the at least one mechanical signal comprises at least one of a stress signal, a thermal signal and an acoustic signal.

16. A system as in claim 1, wherein each of the sensor devices is coupled with one of the processors via a wireless connection.

17. A system as in claim 1, wherein the at least one connector connects each of the processors to at least one of a common display device, at least one digital pager, at least one handheld wireless device, an Ethernet connection, an Internet connection and an intranet connection.

18. A system as in claim 1, wherein each of the sensor devices is coupled with one of the processors via a second connector comprising means for detecting at least one of a type of sensor device coupled with the processor and a number of times the sensor device has been used.

19. A system as in claim 18, wherein the second connector further comprises means for activating the sensor device.

20. A system for passively monitoring multiple patients, the system comprising:
    a plurality of sensor devices, each sensor device comprising:
        a surface for coupling with the patient; and
        at least two piezoelectric sensors coupled with the surface for sensing at least one mechanical signal from a patient;
    a plurality of processors, each processor coupled with one sensor device for converting the at least one mechanical signal into at least one digital signal and for comparing digital signals corresponding to each of the at least two piezoelectric sensors to provide data pertaining to the patient; and at least one connector coupled with each processor for connecting each processor with a common apparatus for providing the patient data for the multiple patients to a user;

wherein each sensor device further includes a sheath for containing at least a portion of the surface to provide a protective layer between the surface and the patient, the sheath including at least one sheath-surface connector mounted on the sheath for providing a detachable connection between the sheath and the surface, and wherein the surface must be connected with the sheath via the sheath-surface connector in order to monitor the at least one mechanical signal of the patient.

21. Apparatus for passively monitoring multiple patients, comprising:

a plurality of sensor devices, each sensor device being disposed on a patient support and having a surface for coupling with a patient on the support for sensing at least one mechanical signal from the patient;

a plurality of processors, each processor coupled with one sensor device and being operative for converting the at least one mechanical signal into at least one digital signal and for analyzing the digital signal to extract vital signs and position data pertaining to the patient;

a plurality of displays, each display coupled with one processor and being housed with the processor in a common unit adjacent the support for displaying the vital signs data;

at least one connector coupled with each processor for connecting each processor with a common alarm system for providing an alarm for each of the multiple patients at a location remote from the patient;

wherein the processors are configured to provide an alarm activation signal for activating an alarm based on vital signs or position criteria pertaining to the particular patient.

22. Apparatus as in claim 21, wherein each sensor device is disposed on a different bed for coupling with a patient lying on the bed.

23. Apparatus as in claim 21, wherein each sensor device is disposed on a different chair for coupling with a patient sitting in the chair.

24. Apparatus as in claim 21, wherein each sensor device is configured to couple with the patient through at least one layer of clothing, bedding or other material.

25. Apparatus as in claim 21, wherein each sensor device is configured to couple with a patient in a general care area of a hospital, in a long-term care facility, or in a nursing home.

26. Apparatus as in claim 21, wherein each sensor device is configured to couple with a patient undergoing a surgical procedure under conscious sedation.

27. Apparatus as in claim 21, wherein each sensor device includes a plurality of sensors disposed in an array.

28. Apparatus as in claim 21, wherein each sensor device has at least two piezoelectric sensors.

29. Apparatus as in claim 28, wherein each of said sensors comprises a polarized polymer film with piezoelectric properties.

30. Apparatus as in claim 28, wherein the piezoelectric sensors are selected from the group consisting of polyvinylidene fluoride film, polyvinylidene cable, piezoelectric ceramic disks and piezoelectric foam.

31. Apparatus as in claim 21, wherein each sensor device has at least two piezoelectric sensors for sensing a first mechanical signal from the patient with the first piezoelectric sensor and a second mechanical signal from the patient with the second piezoelectric sensor.

32. Apparatus as in claim 31, wherein each processor is coupled with the piezoelectric sensors in a respective one of the sensor devices, and is configured for converting the first and second mechanical signals into first and second digital signals and for comparing the first and second digital signals to extract the patient vital signs data based on the comparison of the digital signals.

33. Apparatus as in claim 31, wherein each of the piezoelectric sensors comprises a thin rectangular strip of polarized polymer film with piezoelectric properties, the strips being arranged on the surface in a pattern that runs laterally across the surface.

34. Apparatus as in claim 32, wherein each processor extracts vital signs data in the form of heart rate based on the comparison of the digital signals.

35. Apparatus as in claim 32, wherein each processor extracts vital signs data in the form of respiration rate based on the comparison of the digital signals.

36. Apparatus as in claim 32, wherein each processor extracts vital signs data in the form of heart rate and respiration rate based on the comparison of the digital signals.

37. Apparatus as in claim 32, wherein each processor is further operative to extract information about patient movement based on the comparison of the digital signals, and to provide an alarm activation signal for activating said alarm if the digital signals suggest that the patient is not moving on the surface, the patient is not in contact with the surface, or the patient is moving excessively on the surface.

38. Apparatus as in claim 21, wherein the at least one mechanical signal comprises at least one of a stress signal, a thermal signal, and an acoustic signal.

39. Apparatus as in claim 21, wherein each display is configured to display said vital signs data in numerical form.

40. Apparatus as in claim 21, wherein each display is configured to display said vital signs data in graphical form.

41. Apparatus as in claim 21, wherein each sensor device is disposed on a different bed for coupling with a patient lying in the bed, and the display associated with the sensor device is placed in a bedside location.

42. Apparatus as in claim 21, wherein the at least one connector comprises a wireless transmitter.

43. Apparatus as in claim 21, wherein each processor activates the alarm associated with a particular patient if a respiration rate of the patient falls below a pre-defined minimum respiration rate or rises above a pre-defined maximum respiration rate.

44. Apparatus as in claim 21, wherein each processor activates the alarm associated with a particular patient if a heart rate of the patient falls below a pre-defined minimum heart rate or rises above a pre-defined maximum heart rate.

45. Apparatus as in claim 21, wherein each processor is further operative to compare the at least one digital signal to at least one earlier digital signal for recognizing a trend in the vital signs data based on the comparison of the digital signal to the earlier digital signal, and to provide an alarm activation signal when the trend in the vital signs data matches a pre-defined negative trend.

46. Apparatus as in claim 45, wherein each processor is operative to compare at least one heart beat signal to at least one earlier heart beat signal and at least one respiration signal to at least one earlier respiration signal and to provide an alarm activation signal when the negative trend comprises a combination of a negative heart beat trend and a negative respiration trend.

47. Apparatus as in claim 21, wherein each processor provides an alarm activation signal if a combination of at least two vital signs parameters do not meet pre-defined thresholds associated with those parameters.

48. Apparatus as in claim 21, wherein the at least one connector is configured for coupling the processor with a pre-existing alarm system in a hospital, long-term care facility or nursing home.

49. Apparatus as in claim 21, wherein the at least one connector is configured for coupling the processor with a nurse call system in a hospital.

50. Apparatus as in claim 49, wherein the nurse call system is configured to activate an alarm located outside a room in which the particular patient is located.

51. Apparatus as in claim 49, wherein the nurse call system is configured to activate an alarm at a nurse call station.

52. Apparatus as in claim 21, wherein each of the multiple patients is monitored simultaneously.

53. Apparatus as in claim 21, wherein each of the processors simultaneously provides vital signs data corresponding to the multiple patients to a user at a central location.

54. Apparatus as in claim 21, wherein each of the processors is coupled with a common display device disposed at a central location for displaying vital signs data corresponding to the multiple patients.

55. Apparatus as in claim 54, wherein the central location comprises a nursing station on the general care floor of a hospital.

56. Apparatus as in claim 21, wherein each display is configured to display patient data on a monitor in the form of the patient's heart rate and respiration rate in both numerical and graphical form, and further including multiple local alarms, each local alarm coupled with one processor and disposed adjacent one patient to provide an alarm indication whenever at least one of the digital signals does not meet at least one pre-defined threshold.

57. Apparatus as in claim 21, wherein each of the processors operates continuously around the clock.

58. A system for passively monitoring multiple patients, the system comprising:
a plurality of sensor devices, each sensor device being adapted to be disposed on a patient support and comprising at least two sensors for sensing at least one mechanical signal from the patient;
a plurality of processors, each processor coupled with one sensor device and being operative for converting the at least one mechanical signal into at least one digital signal and for analyzing the digital signals to select the sensors with the highest quality heart rate and respiration rate signals to use for deriving heart rate and respiration rate data pertaining to the patient; and
at least one connector coupled with each processor for connecting each processor with a common alarm system for providing an alarm based on heart rate and/or respiration rate criteria for each of the multiple patients to a user at a remote location.

59. A system as in claim 58, wherein each sensor device comprises a flat pad adapted to be placed on a bed under one or more layers of bedding.

60. A system as in claim 59, wherein the flat pad comprises at least one layer of a resilient foam material.

61. A system as in claim 58, wherein each of the sensors comprises a piezoelectric sensor.

62. A system as in claim 58, wherein each sensor device further includes a removable sheath for containing at least a portion of the sensor device to provide a protective layer between the sensor device and the patient.

63. A system as in claim 58, wherein the at least one mechanical signal comprises at least one of a stress signal, a thermal signal and an acoustic signal.

64. A system as in claim 58, wherein each of the processors is further operative to provide data indicating the presence or absence of the patient on the patient support surface.

65. A system as in claim 58, wherein each processor is further operative to compare the at least one digital signal to at least one earlier digital signal for recognizing a trend in the heart rate or respiration rate data based on the comparison of the digital signal to the earlier digital signal, and to provide an alarm activation signal when the trend in the data matches a pre-defined negative trend.

66. A system as in claim 58, wherein each processor is further operative to extract information about patient movement, and to provide an alarm activation signal for activating said alarm if the digital signals suggest that the patient is not moving on the surface, the patient is not in contact with the surface, or the patient is moving excessively on the surface.

67. A system as in claim 58, wherein the at least one connector is configured for coupling the processor with a pre-existing alarm system in a hospital, long-term care facility or nursing home.

68. A system as in claim 58, wherein each of the processors is coupled with a common display device disposed at a central location for displaying the heart rate and respiration rate data corresponding to the multiple patients, the central location comprising a nursing station on the general care floor of a hospital.

69. A system as in claim 58, further comprising a plurality of displays, each display being coupled with an individual one of the processors and being located adjacent a patient, wherein each display is configured to display patient data on a monitor in the form of the patient's heart rate and respiration rate in both numerical and graphical form.

70. A system for passively monitoring multiple patients, the system comprising:
a plurality of sensor devices, each sensor device being adapted to be disposed on a patient support and comprising at least two sensors for sensing at least one mechanical signal from the patient;
a plurality of processors, each processor coupled with one sensor device and being operative for converting the at least one mechanical signal into at least one digital signal and for comparing digital signals corresponding to each of the at least two sensors to each other to derive data pertaining to the patient in the form of heart rate and respiration rate; and
at least one connector coupled with each processor for connecting each processor with a common alarm system for providing an alarm based on heart rate and/or respiration rate criteria for each of the multiple patients to a user at a remote location.

71. A system as in claim 70, wherein each sensor device comprises a flat pad adapted to be placed on a bed under one or more layers of bedding.

72. A system as in claim 71, wherein the flat pad comprises at least one layer of a resilient foam material.

73. A system as in claim 70, wherein each of the sensors comprises a piezoelectric sensor.

74. A system as in claim 70, wherein each sensor device further includes a removable sheath for containing at least a portion of the sensor device to provide a protective layer between the sensor device and the patient.

75. A system as in claim 70, wherein the at least one mechanical signal comprises at least one of a stress signal, a thermal signal and an acoustic signal.

76. A system as in claim 70, wherein the sensor device has at least two sensors for sensing a first mechanical signal with the first sensor and a second mechanical signal with the second sensor; and wherein each of the processors is operative to compare the digital signals by comparing presence or absence of the first signal with presence or absence of the second signal.

77. A system as in claim 70, wherein each of the processors is further operative to provide data indicating the presence or absence of the patient on the patient support surface.

78. A system as in claim 70, wherein each processor is further operative to compare the at least one digital signal to at least one earlier digital signal for recognizing a trend in the heart rate and respiration rate data based on the comparison of the digital signal to the earlier digital signal, and to provide an alarm activation signal when the trend in the data matches a pre-defined negative trend.

79. A system as in claim 70, wherein each processor is further operative to extract information about patient movement based on the comparison of the digital signals, and to provide an alarm activation signal for activating said alarm if the digital signals suggest that the patient is not moving on the surface, the patient is not in contact with the surface, or the patient is moving excessively on the surface.

80. A system as in claim 70, wherein the at least one connector is configured for coupling the processor with a pre-existing alarm system in a hospital, long-term care facility or nursing home.

81. A system as in claim 70, wherein each of the processors is coupled with a common display device disposed at a central location for displaying heart rate and respiration rate data corresponding to the multiple patients, the central location comprises a nursing station on the general care floor of a hospital.

82. A system as in claim 70, further comprising a plurality of displays, each display being coupled with an individual one of the processors and being located adjacent a patient, wherein each display is configured to display patient data on a monitor in the form of the patient's heart rate and respiration rate in both numerical and graphical form.

\* \* \* \* \*

UNITED STATES PATENT AND TRADEMARK OFFICE
CERTIFICATE OF CORRECTION

PATENT NO. : 7,666,151 B2
APPLICATION NO. : 10/301524
DATED : February 23, 2010
INVENTOR(S) : Sullivan et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 948 days.

Signed and Sealed this

Twenty-eighth Day of December, 2010

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,666,151 B2 | Page 1 of 1 |
| APPLICATION NO. | : 10/301524 | |
| DATED | : February 23, 2010 | |
| INVENTOR(S) | : Patrick K. Sullivan et al. | |

It is certified that error appears in the above-identified patent and that said Letters Patent is hereby corrected as shown below:

Column 12, line 7, after "invention" delete "n" and insert instead --on--.

Column 14, line 23, after "example," insert --a--.

Column 16, line 44, after "allow" insert --the--.

Column 17, line 45, after "at" insert --a--.

Column 18, line 15, before "display" insert --the--.

Column 19, line 15, delete "formed" and insert instead --former--.

Signed and Sealed this
Twenty-second Day of February, 2011

David J. Kappos
*Director of the United States Patent and Trademark Office*